US010535430B1

(12) United States Patent
Fischer et al.

(10) Patent No.: US 10,535,430 B1
(45) Date of Patent: Jan. 14, 2020

(54) METHOD AND SYSTEM FOR GROUPING MEDICAL CLAIMS

(71) Applicant: INTERNATIONAL BUSINESS MACHINES CORPORATION, Armonk, NY (US)

(72) Inventors: Anne Elizabeth Fischer, Chelsea, MI (US); Dennis Dunn, Moorestown, NJ (US); Gary Pickens, Wilmette, IL (US); Elisse Jane Moldwin, Evanston, IL (US); Peter Mark Bouman, Chicago, IL (US); George Sirbu, Saline, MI (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 776 days.

(21) Appl. No.: 14/341,253

(22) Filed: Jul. 25, 2014

(51) Int. Cl.
*G06Q 50/22* (2018.01)
*G16H 40/20* (2018.01)

(52) U.S. Cl.
CPC .................... *G16H 40/20* (2018.01)

(58) Field of Classification Search
USPC ......................................................... 705/2–4
See application file for complete search history.

(56) References Cited

U.S. PATENT DOCUMENTS

| | | | | |
|---|---|---|---|---|
| 5,508,912 A * | 4/1996 | Schneiderman | ...... | G06F 19/325 705/3 |
| 5,835,897 A * | 11/1998 | Dang | ...... | G06F 19/328 705/2 |
| 7,912,842 B1 * | 3/2011 | Bayliss | ...... | G06F 17/30303 707/749 |
| 8,340,981 B1 * | 12/2012 | Cave | ...... | G06Q 10/10 705/2 |
| 2007/0106533 A1 * | 5/2007 | Greene | ...... | G06Q 10/10 705/2 |
| 2007/0150315 A1 * | 6/2007 | Bennett | ...... | G06F 19/322 705/3 |
| 2014/0081652 A1 * | 3/2014 | Klindworth | ...... | G06Q 10/10 705/2 |
| 2014/0089012 A1 * | 3/2014 | Lynn | ...... | G06Q 10/00 705/3 |

OTHER PUBLICATIONS

Wilchesky, Machelle, Robyn M. Tamblyn, and Allen Huang. "Validation of diagnostic codes within medical services claims." Journal of clinical epidemiology 57.2 (2004): 131-141.*

* cited by examiner

*Primary Examiner* — Mark Holcomb
(74) *Attorney, Agent, or Firm* — Michael Best & Friedrich LLP

(57) ABSTRACT

A method and system for grouping medical claims data, including outpatient medical claims, into medical events for further analysis is disclosed. Historical outpatient medical claims data is first aggregated by one or more categorization schemes, and then grouped by patient and date. Once the outpatient medical claims data is aggregated and grouped, the methods disclosed build outpatient events by further grouping together disparate medical claims data records that represent a single encounter with an outpatient healthcare system. The outpatient events may be used for analyzing aspects of outpatient care.

25 Claims, 20 Drawing Sheets

| Data Field | Flag |
|---|---|
| Patient ID | |
| Age of Patient | |
| Gender of Patient | |
| Date of Service | |
| Diagnosis Code(s) | ~344 |
| Procedure Code | ~342 |
| Revenue Code | ~346 |
| Claim Type Indicator (Professional/ Facility) | |
| Provider ID | |
| Provider Type | ~348 |
| Place of Service | ~350 |
| Claim ID | |
| Record ID | |
| Allowed Amount | |
| Submitted Charges | |
| Network Indicator | |
| Inpatient Adjacency Indicator | |
| Custom Fields | |

Figure 3

| Priority | Type of Procedures | Examples | # of Procedure Groups |
|---|---|---|---|
| 1 | Inpatient | Coronary Artery Bypass, Organ Transplant, Delivery | 70 |
| 2 | Major Surgical/ Invasive | Arthroscopic Surgeries, Colonoscopy, PTCA | 228 |
| 3 | Major Imaging | CT Scan, MRI | 31 |
| 4 | Minor Surgical/ Invasive | Lymph Node Biopsy, Wound Repair, Myringotomy | 145 |
| 5 | E&M and Minor Diagnostic | Office Visit, Observation Care, Fetal Monitoring | 52 |
| 6 | Radiology | X-Ray, EKG, Angiography | 232 |
| 7 | Laboratory | Pathology, Electrolyte, Chemistry | 26 |
| 8 | Drug Administration | Vaccination Administration, Chemotherapy Administration | 12 |
| 9 | Ancillary/ Additional Services | Anesthesia, Blood, Ambulance | 212 |

Figure 4A

| Body System | Examples | # of Disease Categories |
|---|---|---|
| CVS: Cardiovascular | Arrhythmias, Cardiomyopathies, CHF, AMI | 34 |
| END: Endocrine | Diabetes, Hypothyroidism | 21 |
| ENT: Ear, Nose, Throat | Pharyngitis, Sinusitis, Otitis Media | 24 |
| GIS: Gastrointestinal | Appendicitis, Gastroenteritis, Hernia | 46 |
| MUS: Musculoskeletal | Fracture, Injury, Osteoarthritis | 58 |
| PSY: Psychological | Depression, Anxiety Disorder, Bipolar Disorder | 20 |
| RES: Respiratory | Asthma, Influenza, Pneumonia | 36 |

Figure 4B

| Revenue Category | Range of UB04 Revenue Codes |
|---|---|
| Pharmacy | 250-259 |
| Laboratory | 300-309 |
| Laboratory: Pathology | 310-319 |
| Radiology - Diagnostic | 320-329 |
| CT Scan | 350-359 |
| Operating Room Services | 360-369 |
| Anesthesia | 370-379 |
| Physical Therapy | 420-429 |
| Cardiology | 480-489 |
| Ambulatory Surgery Care | 490-499 |
| MRI | 610-619 |
| EKG / ECG | 730-739 |
| ... | ... |

900

| | | 822 | 818 | 820 | 830 | 806 |
|---|---|---|---|---|---|---|
| 901 | First Phase Criteria | 1 | 2 | 3 | 4 | 5 |
| 902 | Record Procedure Group ⟷ Anchor Procedure Group | If related (912) | If strongly related (914) | If strongly related (916) | If very strongly related (918) | No (920) |
| 904 | Record Principal Disease Category ⟷ Anchor Procedure Group | If related | If related | If record procedure missing and very strongly related | No | No |
| 906 | Record Revenue Category ⟷ Anchor Procedure Group | If related | If related | If record procedure missing and very strongly related | No | No |
| 908 | Record Revenue Category Anchor Procedure AND Record Disease Category ⟷ Anchor Procedure Group | N/A | N/A | If record procedure missing and both strongly related | No | No |
| 910 | Record Secondary Disease Category ⟷ Anchor Procedure Group | If strongly related | If strongly related | No | No | No |

| | | 822 | 818 | 820 | 830 | 806 |
|---|---|---|---|---|---|---|
| 951 | Secondary Phase Criteria | 1 | 2 | 3 | 4 | 5 |
| 952 | Include Record if Provider ID Matches any other Provider ID in Event | Yes | Yes | Yes | No | No |
| 954 | Include Record if Claim ID Matches any other Claim ID in Event | Yes | Yes | Yes | Yes | Only facility |

Figure 9B

| Procedure Group | P-value | Lift ratio |
|---|---|---|
| Laparoscopy, Surgical, Appendix | 0.00 | 1541 |
| Anesthesia, Complicated | 0.00 | 254 |
| Anesthesia - Lower Abdomen | 0.00 | 39 |
| Emergency Department Visit, Emergent | 0.00 | 38 |
| CT - Abdomen | 0.00 | 17 |
| Observation Care Discharge | 0.00 | 15 |
| Lab - Surgical Path | 0.00 | 12 |
| Injectables - Anesthetics | 0.00 | 9 |
| Supplies | 0.00 | 6 |
| Lab - Urinalysis | 0.00 | 4 |
| Anesthesia - Upper Abdomen | 0.00 | 3 |
| Lab - Basic Metabolic Panel | 0.00 | 3 |
| X-ray - Abdomen | 0.00 | 3 |
| Office Medical Visit, New Patient | 0.00 | 3 |
| Ultrasound, Abdomen | 0.00 | 2 |
| Lab - Chemistry | 0.00 | 1 |
| Lab - Creatinine | 0.93 | 1 |
| X-Ray - Chest | 1.00 | 1 |

Figure 10A

| Disease Category | P-value | Lift ratio |
|---|---|---|
| Appendicitis | 0.00 | 5243 |
| Endometriosis | 0.00 | 53 |
| Anomaly: Other Digestive or Hepatobiliary System | 0.00 | 51 |
| Other Diseases of Esophagus, Stomach, and Duodenum | 0.00 | 48 |
| Other Gastrointestinal Infections | 0.00 | 34 |
| Other Gastrointestinal or Abdominal Symptoms | 0.00 | 26 |
| Other Biliary Disorders | 0.00 | 19 |
| Anomaly: Uterus | 0.00 | 10 |
| Other Gastrointestinal Disorders | 0.00 | 9 |
| Neoplasm, Benign: Other Gastrointestinal System | 0.00 | 7 |
| Pancreatitis | 0.00 | 6 |
| Calculus of the Urinary Tract | 0.00 | 2 |
| Abnormal Lab, X-ray and Clinical Findings | 0.00 | 1 |
| Ectopic Pregnancy | 0.19 | 2 |
| Neoplasm, Malignant: Other Female Genitalia | 0.22 | 2 |
| Anomaly: Other Genitalia | 0.40 | 1 |
| Food Poisoning: Other Organisms | 0.54 | 1 |
| Anomaly: Defects of Kidney | 0.55 | 1 |

Figure 10B

| |
|---|
| Patient ID |
| Gender |
| Age |
| Custom Patient Characteristics |
| Event ID |
| Start Date |
| End Date |
| Days |
| Anchor Procedure Group Code |
| Event Label |
| Rollup Category |
| Principal Procedure Code |
| Principal Diagnosis Code |
| Total Allowed Amount |
| Professional Allowed Amount |
| Facility Allowed Amount |
| Type of Claims Included (Facility/ Professional) |
| Site of Service |
| Inpatient Adjacent Indicator |
| Percent of Charges Paid at In-Network Rates |
| Exception Code for Event |
| Primary Provider - Professional |
| Primary Provider Type - Professional |
| Count of Professionals |
| Primary Provider - Facility |
| Primary Provider Type - Facility |
| Count of Facilities |
| Emergency Department Indicator |
| Anesthesia Indicator |
| Professional Office Visit Indicator |
| Major Surgery/ Invasive Procedure Indicator |
| Major Procedure Group Count |
| Major Procedure CPT/ HCPCS Procedure Code Count |
| Major Imaging Procedure Indicator |
| Major Imaging Procedure Count |
| Major Imaging CPT/ HCPS Procedure Code Count |

1100

1102 — Patient ID through Custom Patient Characteristics

1104 — Event ID through Exception Code for Event

1106 — Primary Provider - Professional through Count of Facilities

1108 — Emergency Department Indicator through Major Imaging CPT/ HCPS Procedure Code Count

Figure 11

| Claim Record ID# | Procedure Code | Procedure Group | Sort Order | Reason Code |
|---|---|---|---|---|
| Claim Record ID (1) | Procedure Code (1) | Procedure Group (1) | Sort Order (1) | Reason Code (1) |
| Claim Record ID (2) | Procedure Code (2) | Procedure Group (2) | Sort Order (2) | Reason Code (2) |
| Claim Record ID (n) | Procedure Code (n) | Procedure Group (n) | Sort Order (n) | Reason Code (n) |
| Claim Record ID (...) | Procedure Code (...) | Procedure Group (...) | Sort Order (...) | Reason Code (...) |

Figure 12

METHOD AND SYSTEM FOR GROUPING MEDICAL CLAIMS

BACKGROUND OF THE INVENTION

Technical Field

The present disclosure relates generally to methods for grouping medical claims data for more accurately analyzing medical care.

Background

With the increasing complexity in healthcare systems and the rising costs of delivering healthcare, the need to review and analyze medical claims data across a variety of healthcare providers and facilities is becoming more important. Furthermore, with the rising number of healthcare procedures taking place in an outpatient setting, the need to isolate the outpatient medical claims data is more pronounced, and the benefits of being able to combine related outpatient medical claims data to more accurately analyze outpatient providers and facilities is more evident. However, because of the numerous outpatient providers, analyzing outpatient events based on straight administrative claims data presents a number of limitations.

One difficulty in analyzing outpatient medical claims data relates to the number of claims that can be generated for a single outpatient procedure. For example, for a single outpatient encounter, a professional and a facility provider may each submit their own claim for payment. In addition, there may be a separate lab claim, and a separate pharmaceutical claim, in addition to other types of claims. Each claim usually reflects the information required for payment to the particular provider submitting the claim. This information may not include the most detailed or accurate clinical information, leaving a potential question as to what precise procedure might have been carried out or what the underlying medical condition was.

Another difficulty in analyzing outpatient medical claims is that the outpatient medical claims data can lack sufficient detail, particularly when it is obtained from multiple sources with varying degrees of quality control. For example, certain types of professional claims, such as radiology or pathology interpretations often include inaccurate place of service information, that is, rather than reflecting where the patient received the imaging service, they might reflect the location of the radiologist or pathologist providing the interpretation. In addition, claims data having missing or invalid procedure codes, inaccurate place of service codes, missing diagnosis codes, etc., can create inconsistencies and errors when performing an analysis on outpatient care.

Another difficult aspect of analyzing outpatient care stems from the fact that patients are not confined to a single location and may receive various types of care in different settings on a given day. In addition, a patient's outpatient service may actually span more than one day, particularly in the case of emergency care visits or hospital outpatient major surgeries. These nuances prevent the assumption that all outpatient data on a given day is related to one and only one outpatient event.

Additionally, when multiple procedures are performed during the same clinical event, the event may have a significantly different price profile than if either procedure was performed alone. For example, when a colonoscopy is completed in combination with an upper gastro-intestinal endoscopy, the outpatient facility may include charges for both procedures on one medical claim. It can be difficult, however, to separate out such combination procedures for analysis or to focus analysis on just the combination procedures when desired.

SUMMARY

In one aspect, the disclosure provides a method for grouping medical claims data for analysis. In particular, a processor receives a plurality of medical claims data records, each comprising a plurality of data fields. The processor then sorts the plurality of medical claims data records by at least one grouping scheme which examines at least one data field in each of the plurality of medical claims data records. Next, the processor builds at least one dateblock from the plurality of medical claims data records. To build the at least one dateblock, the processor first examines a patient data field and a date data field in each of the plurality of medical claims data records and groups the medical claims data records together by a first patient and a first date. The processor next sorts, by the first date, the medical claims data records grouped by the first patient into the at least one dateblock. After building the at least one dateblock, the processor prioritizes, within the at least one dateblock, the medical claims data records according to the at least one grouping scheme to identify a first priority medical claims data record. The processor then assigns the procedure associated with the first priority medical claims data record as an anchor procedure for a first medical event. The processor next reviews, within the at least one dateblock, the remaining medical claims data records to identify the remaining medical claims data records that match the anchor procedure for the first medical event. Finally, the processor builds, from the medical records in the at least one dateblock, a first medical event that comprises the first priority medical claims data record and the set of the remaining medical claims data records that match the anchor procedure for the first medical event.

In another aspect, the disclosure provides a system for analyzing outpatient medical claims data. The system comprises a database having outpatient medical claims data from multiple claims data sources and a server coupled to the database. Within the system, the server is configured to receive a plurality of outpatient medical claims data records from the database, wherein each data record comprises a plurality of data fields. The server then sorts the plurality of outpatient medical claims data records by at least one grouping scheme, which examines at least one data field in each of the plurality of outpatient medical claims data records. Next, the server builds at least one dateblock from the plurality of outpatient medical claims data records. To build the at least one dateblock, the server examines both a patient data field and a date data field in each of the plurality of outpatient medical claims data records and groups the outpatient medical claims data records together by a first patient and a first date. Next, the server sorts the outpatient medical claims data records grouped by the first patient into at least one dateblock. After building the at least one dateblock, the server prioritizes the outpatient medical claims data records within the dateblock according to the at least one grouping scheme. During the prioritizing step, the server identifies an outpatient medical claims data record having a first priority. The server then assigns the procedure associated with the outpatient medical claims data record having the first priority as an anchor procedure for a first outpatient event. After the anchor procedure is identified, the server reviews the remaining outpatient medical claims data records in the dateblock to identify which of the remaining outpatient medical claims data records match the anchor procedure. The server then builds a first outpatient event in the first dateblock, wherein the first outpatient event comprises the first priority outpatient medical claims data record and the set of the remaining outpatient medical claims data records that match the anchor procedure for the first outpatient event.

In yet another aspect, the disclosure provides a non-transitory computer-readable medium comprising computer-readable instructions for performing the steps associated with grouping medical claims data for analysis. In particular, the steps involved begin with receiving a plurality of outpatient medical claims data records at a processor. Next, a portion of the plurality of outpatient medical claims data records are grouped by the processor according to a first grouping scheme. The processor then aggregates the plurality of outpatient medical claims data records by date to create a plurality of dateblocks, wherein each of the plurality of dateblocks comprises a subset of the plurality of outpatient medical claims data records. Next, the processor prioritizes, in each of the plurality of dateblocks, the respective subset of the plurality of outpatient medical claims data records. Further, within each of the plurality of dateblocks, the processor determines if a facility component associated with a first outpatient medical claims data record should be linked to a professional component associated with a second outpatient medical claims data record, and if determined, links the associated records. The processor then identifies, at least one anchor procedure in each of the plurality of dateblocks which represents at least one of the outpatient medical claims data records in the respective subset of the plurality of outpatient medical claims data records. Next, the processor applies matching logic to the remaining outpatient medical claims data records to match remaining outpatient medical claims data records in the respective subset of the plurality of outpatient medical claims data records with the anchor procedure outpatient medical claims data record.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments described herein can be better understood with reference to the following figures. The figures are intended to be exemplary and, when read in combination with the description, are provided to explain, and not limit, the present disclosure.

FIG. 3 depicts an example medical claims data record according to an embodiment of the present disclosure;

FIGS. 4A-4E depict examples of grouping schemes that may be used with embodiments described herein;

FIGS. 9A-9B depict examples of relationship scenarios between outpatient medical claims data, according to an embodiment of the present disclosure;

FIGS. 10A-10B depict examples of statistical relationships for a laparoscopic appendectomy procedure, according to an embodiment of the present disclosure FIG. 11 depicts an example of an output data record for an outpatient medical event, constructed according to an embodiment of the present disclosure;

FIG. 12 depicts an example of cross-referenced data among grouped outpatient medical claims data, according to an embodiment of the present disclosure.

DETAILED DESCRIPTION

According to embodiments set forth herein, outpatient medical claims data may be processed and aggregated by an enhanced medical claims processing server to group related outpatient medical claims into outpatient events. For purposes of the present disclosure, an outpatient event refers to a grouping of medical claims that represent a single outpatient encounter with the healthcare system for a patient. Outpatient events may be used to analyze aspects of the outpatient system. For example, outpatient event groupings may allow for analysis of the cost of outpatient care, the quality of outpatient care and the efficiency of the outpatient system, among other criteria. As discussed in more detail below, methods described herein provide reliable outpatient claim grouping results by, for example, separating encounters with an outpatient system on a given day that show very low probability of being related, while at the same time including encounters on adjacent days that meet certain probability thresholds for inclusion. In addition, the disclosed methods may take into account anomalies that may be present in the outpatient medical claims data, such as, but not limited to, an inconsistent service site or missing procedural or diagnostic information.

Figure 1:
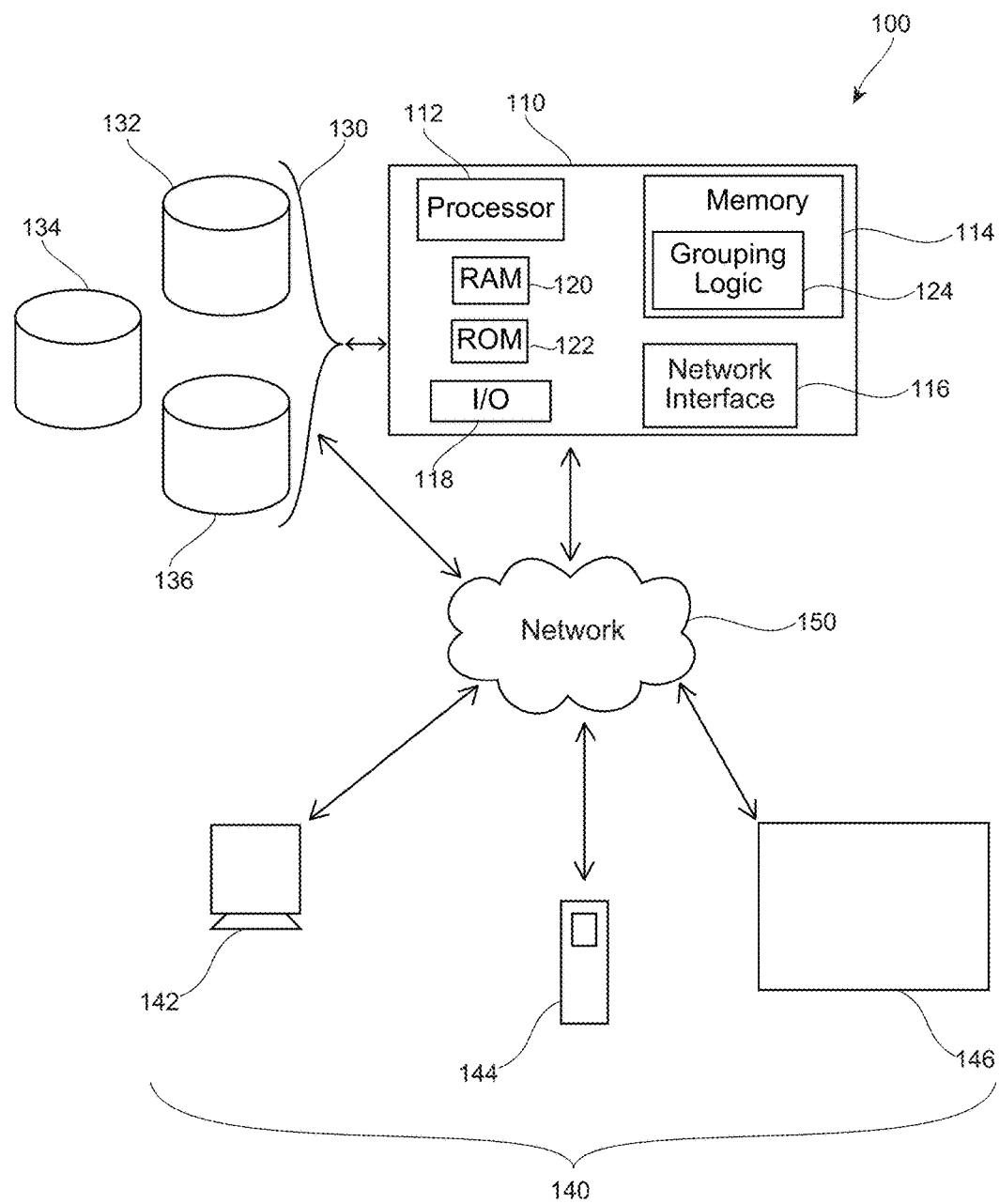
FIG. 1 depicts a network environment in which aspects of the present disclosure may be implemented.

Embodiments of the methods and system described herein may utilize various computer software and hardware components, including but not limited to, servers, mainframes, desktops computers, databases, computer-readable media, input/output devices, networking components and other components as would be known and understood by a person skilled in the art. FIG. 1 illustrates a networked operating environment 100 in which aspects of the present disclosure may be implemented, according to at least one embodiment described herein. It should be understood, however, that environment 100 is only one example of a suitable environment for implementing methods described herein and is not intended to suggest any limitation as to the scope or functionality of the present disclosure. Environment 100 may include one or more servers 110, one or more databases 132, 134, 136, collectively, databases 130, and one or more access devices, such as computer/laptop computer 142, handheld device 144 and enterprise device 146, collectively access devices 140. Components of environment 100 may be connected to one or more networks, such as network 150, for communication between the components.

Server 110 is generally representative of one or more servers suitable for processing medical claims data and serving data in the form of webpages or other markup language forms with associated applets, ActiveX controls, remote-invocation objects, or other related software and data structures, to service clients of various "thicknesses." Server 110 may be configured as would be known by a skilled artisan and may include a processor 112, memory 114, one or more network interfaces 116, one or more input/output devices 118, RAM 120, ROM 122 and a grouping logic module 124 for processing medical claims data.

Processor 112 may include one or more local or distributed processors, controllers, or virtual machines. As would be understood in the art, processor module 112 may be configure in any convenient or desirable form as would be known by a skilled artisan. Memory 114 may comprise one or more electronic, magnetic, or optical data-storage devices, as well as store grouping logic module 124. As would be known in the art, memory 114 may store instructions, such as grouping logic module 124, for processing by processor 112. Grouping logic module 124 may include machine readable and/or executable instructions sets for performing and/or facilitating performance of methods and rendering graphical user interfaces as further described herein, including sharing one or more portions of this functionality in a client-server architecture, over a wireless or wireline communications network 150 with one or more access devices 140. The grouping logic may be embodied in a variety of known software systems, including but not limited to, SAS® and Java®.

Databases 130 may include one or more separate databases, such as database 132, database 134 and database 136. Further, as would be understood in the art, each of databases 130 may include one or more electronic, magnetic, optical data-storage devices, or other data-storage devices which can include or are otherwise associated with respective indices (not shown). In some embodiments, databases 130 include medical, drug, and lab-related medical claims data. In other embodiments, databases 130 include and/or extract healthcare administrative data, such as medical claims and encounter data, from health plan, employer and government databases. In at least one embodiment, medical claims data types include data related to outpatient care including, but not limited to, outpatient facility claims, such as a hospital outpatient department facility, a skilled nursing facility, and so on; outpatient professional claims; and/or other claims, such as from durable medical equipment suppliers, workers compensation, short and long term disability, drug claims, and so forth. In some embodiments, databases 130 additionally include medical guidelines data sources, such as government and/or other public sources, government regulations and proprietary databases, as further discussed below. According to aspects described herein, databases 130 may be connected to server 110 via a network 150.

Server 110 may be accessed by one or more access devices, including, but not limited to, personal computers, enterprise workstations, handheld devices, mobile telephone, or any other device capable of providing an effective user interface with a server or database. As depicted, in at least one embodiment, server 110 is connected to one or more access devices 140 via network 150.

As depicted, server 110 may include processor 112 which may further include one or more processors, processing circuits, or controllers. Processor 112 may be coupled to memory 114, which stores code (machine-readable or executable instructions) for server 110, as well as for processes performed by server 110. In at least one embodiment, memory 114 includes a grouping logic module 124 which may include computer-executable instructions for processing various medical claims data. In addition, as would be understood by those skilled in the art, server 110 may include additional components for operation, such as RAM 120, ROM 122 and/or input/out mechanisms 118 (such as a keyboard, mouse, display, etc.).

Figure 2:
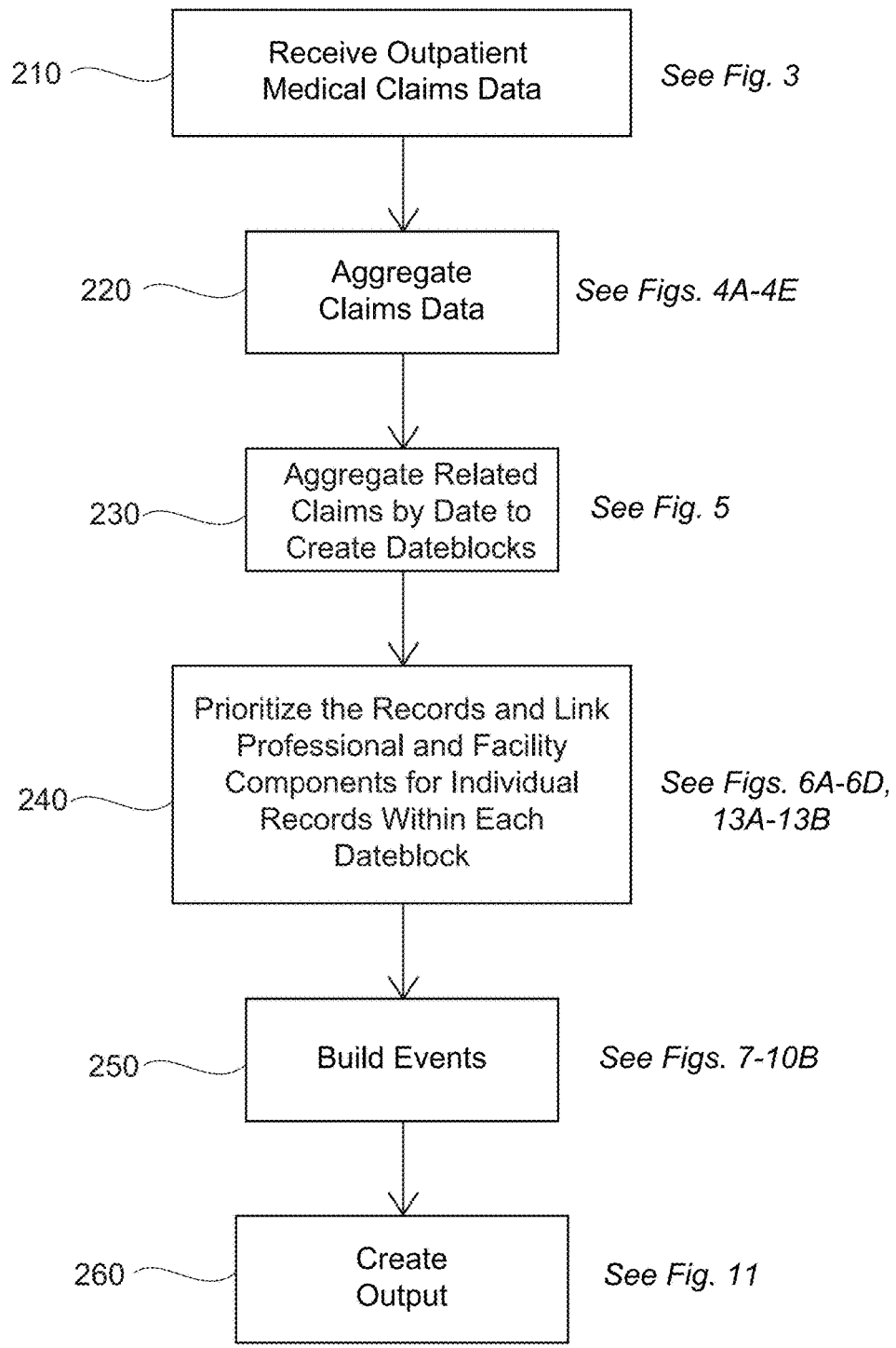
FIG. 2 depicts a flowchart of a method for grouping outpatient medical claims data, according to an embodiment of the present disclosure.

FIG. 2 depicts a flowchart of at least one embodiment of an overall method for grouping outpatient medical claims data according to techniques further described herein. According to at least one embodiment, at step 210, a server or other computer processor may first receive and use as input a plurality of medical claims data records. The medical claims data records may take a variety of forms and structures, as further discussed below. According to at least one embodiment, the medical claims data records may include a plurality of historical outpatient medical claims data. At step 220, the process may aggregate the claims data that is received at step 210 in one or more ways, including, but not limited to, by one or more of the following criteria: the type of procedure and priority of procedure related to each medical claim; the disease category related to each medical claim; standard revenue categories related to each medical claim; the type of provider servicing the patient as related to each medical claim; and the place of service of each medical claim.

After the medical claims data is aggregated, at step 230 the method continues by organizing the medical claims data into one or more dateblocks. As described in more detail below, a dateblock represents one day or a series of consecutive days, each of which includes at least one outpatient encounter, for the same patient. Within each dateblock, according to aspects described herein, at step 240, the process includes prioritizing the medical claims records within each dateblock to ensure that 'high priority' records are addressed first. Also at step 240, the medical claims data may be analyzed further to link medical facility claim components and professional claim components for a given procedure in each dateblock. Once the initial data aggregation and the initial facility/professional linking is accomplished, during the next step, step 250, the actual outpatient events may be created from the medical claims data. As described in more detail below, an outpatient event represents a grouping of outpatient medical claims that represent a single outpatient encounter with the healthcare system. After the outpatient events are built in step 250, at step 260 one or more output data structures or files may be created which detail aspects of the one or more outpatient events that were created and further link all of the medical claims data at the event level. The overall process as depicted in FIG. 2 is described in more detail in the following sections.

Input Medical Claims Data

As set forth at step 210 of FIG. 2, according to some embodiments, an enhanced medical processing server or processor, such as server 110, may receive a plurality of outpatient medical claims data records from one or more databases, such as databases 130, for processing according to techniques described herein. Outpatient medical claims data records may represent claims filed by a healthcare provider related to an outpatient encounter with the healthcare system. Such data records may include data regarding various components of an outpatient encounter, such as data related to one or more professional claims, facility claims, laboratory claims and/or pharmaceutical claims, or other components as would be understood by those skilled in the art. In some cases, various components of an outpatient encounter may be grouped together in one medical claims data record. In other cases, each component may be billed separately. In still other cases, certain claim components of an outpatient encounter, such as a professional provider component, may have multiple claims data records associated with the same outpatient encounter.

An outpatient medical claims data record typically contains data related to the specific patient that was treated and/or to the outpatient encounter to which the data record belongs. The type of data contained in the record will be dependent on the source of the data record, but may include data about one or more of the following: the patient; date(s) of service; diagnosis; procedure(s) performed; provider(s); place of service; charges; and other data related to the outpatient encounter. In some cases, the data record may contain a number of standardized medical billing codes such as UB-04 revenue codes, ICD-9 diagnosis codes, CPT/HCPC procedure codes, and other standard codes as would be understood in the art. FIG. 3 depicts an example medical claims data record 300. As depicted in FIG. 3, a medical claims data record may contain one or more of the following data fields 340: a patient ID field 302; a patient age field 304; a patient gender field 306; a date of service field 308; a diagnosis code field 310; a procedure code field 312; a revenue code field 314; a claim type indicator field 316 (i.e. professional or facility claim type); a provider ID field 318; a provider type field 320; a place of service field 322; a claim ID field 324; a record ID field 326; an allowed amount field 328; a submitted charges field 330; a network indicator field 332; an inpatient adjacency indicator field 334; and one or more custom fields 336. The medical claims data record may also contain a flag field 338 for further information or groupings to be made in relation to one or more of data fields 340. It should be understood, however, that medical claims data record 300 shown in FIG. 3 is only exemplary, and depending on the source of a data record, more or fewer fields may be present and the data record may be structured differently and may include additional data not specifically set forth herein.

There are a number of databases and repositories that can provide historical outpatient medical claims data records, such as example claim data record 300, for use with methods and techniques described herein. For example, in some embodiments, historical Medicare claims data may be used for analysis. In other cases, a commercial source of outpatient medical claims data may be used. In at least one case, historical outpatient claims data records are obtained from the MarketScan® databases produced by Truven Health Analytics, Inc.

Process Medical Claims Data

Referring to step 220 of FIG. 2, after the medical claims data is received in step 210, according to at least some embodiments described herein, the outpatient medical claims data records may be aggregated or grouped based on a variety of categorization schemes. The grouping of the data according to the categorization schemes may facilitate prioritization of the data records once the process of building the outpatient events begins at step 250 of FIG. 2.

According to aspects of the disclosure, the medical claims data records may be grouped or assigned to categorization schemes in a number of ways. In some cases, the medical claims data records may be grouped or flagged based on one or more of: a procedure grouping scheme based on a procedure code in a data record; a disease category grouping scheme based on a diagnosis code in a data record; a revenue code scheme based on a revenue code in a data record; a provider type grouping scheme based on a provider type provided in a data record; and a place of service grouping scheme based on a place of service code provided in a data record. According to at least one embodiment, the medical claims data records may be grouped or assigned to categorization schemes such as the schemes shown in the embodiments of FIGS. 4A-4E. However, it will be understood that a variety of other categorization schemes may also be used and still fall within the spirit and scope of the present disclosure.

In at least one embodiment, each medical claims data record to be processed according to methods described herein may be assigned to a procedure grouping scheme. FIG. 4A depicts an example of a procedure categorization scheme 400 that groups all standard CPT procedure codes into approximately 1000 prioritized groupings. The breakdown of the 1000 groupings according to procedure categorization scheme 400 is shown by the "# of Procedures Groups" 406. For example, according to the example grouping scheme of FIG. 4A, 70 of the approximately 1000 groupings may constitute an "inpatient" procedure.

According to the procedure categorization scheme 400, the procedure groups may be grouped by the "type of procedure" 404, and each "type of procedure" is assigned a "priority level" 402. For example, a coronary artery bypass, an inpatient procedure, would be assigned a priority level 1. Thus, referring back to the example medical claims data record 300 in FIG. 3, flags related to a procedure categorization scheme (such as scheme 400) may be inserted at flag field 342. Further, within each priority level, the procedure groups may be further prioritized to provide more granular prioritization (not shown). As discussed in more detail below, the prioritized grouping assignments to the medical claims data records may be used to prioritize the building of the outpatient events (see step 250 of FIG. 2).

The medical claims data records may also be assigned to a disease category grouping scheme, such as the Disease Staging® classification system from Truven Health Analytics, Inc. However, it will be understood that any other disease categorization scheme contemplated by a skilled artisan may also be used for purposes of the methods described herein. FIG. 4B sets forth the basis of an example of a disease categorization scheme 410 that groups all standard ICD-9/10 diagnosis codes into approximately 600 disease category groupings 412. The breakdown of the 600 groupings is shown by the "# of Disease Categories" 414. For example, according to the example grouping scheme of FIG. 4B, 34 of the approximately 600 groupings may constitute a CVS or cardiovascular "body system" 412 disease category grouping. For example, an arrhythmia diagnosis would be assigned to the CVS or cardiovascular "body system" 412 disease category. Referring to the example medical claims data record 300 in FIG. 3, flags related to a disease category grouping scheme may be inserted at 344. As discussed in more detail below, a disease category grouping scheme may be used to map the diagnosis codes for each individual medical claims data record, which may be examined during the building of the outpatient events (see step 250 of FIG. 2).

Figure 4C:
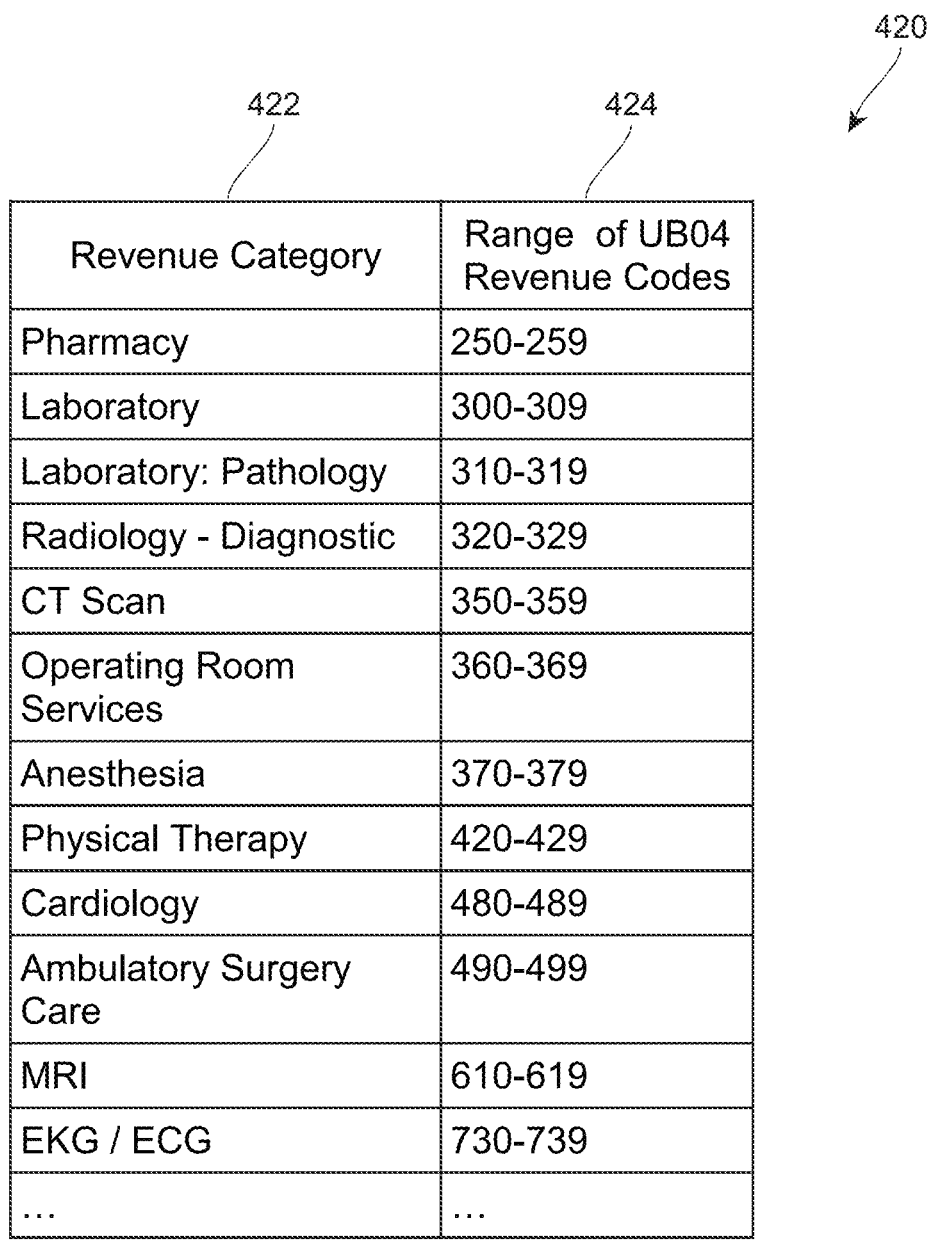

According to aspects of the present disclosure, the medical claims data records may also grouped according a revenue code category grouping scheme. FIG. 4C sets forth the basis of an example of a revenue code categorization scheme 420 that groups all standard UB04 revenue codes into approximately 72 revenue code range groupings (FIG. 4C depicts only a few of the approximately 72 UB04 revenue code groupings). A partial breakdown of the 72 example groupings is shown by the "Range of UB04 Revenue Codes" 424 column in the chart of FIG. 4C. For example, according to the example provider type grouping scheme 430 (see FIG. 4D), pharmacy revenue codes represents at least one "Revenue Category" 422 and may constitute a range of UB04 revenue codes 250-259. Referring to the example medical claims data record 300 in FIG. 3, flags related to a revenue code categorization scheme may be inserted at 346. According to aspects of the disclosure, a revenue code range categorization scheme, such as revenue code categorization scheme 420, may be used to map the revenue code for each individual medical claims data record, which may be examined during the building of the outpatient events (step 250).

Figure 4D:
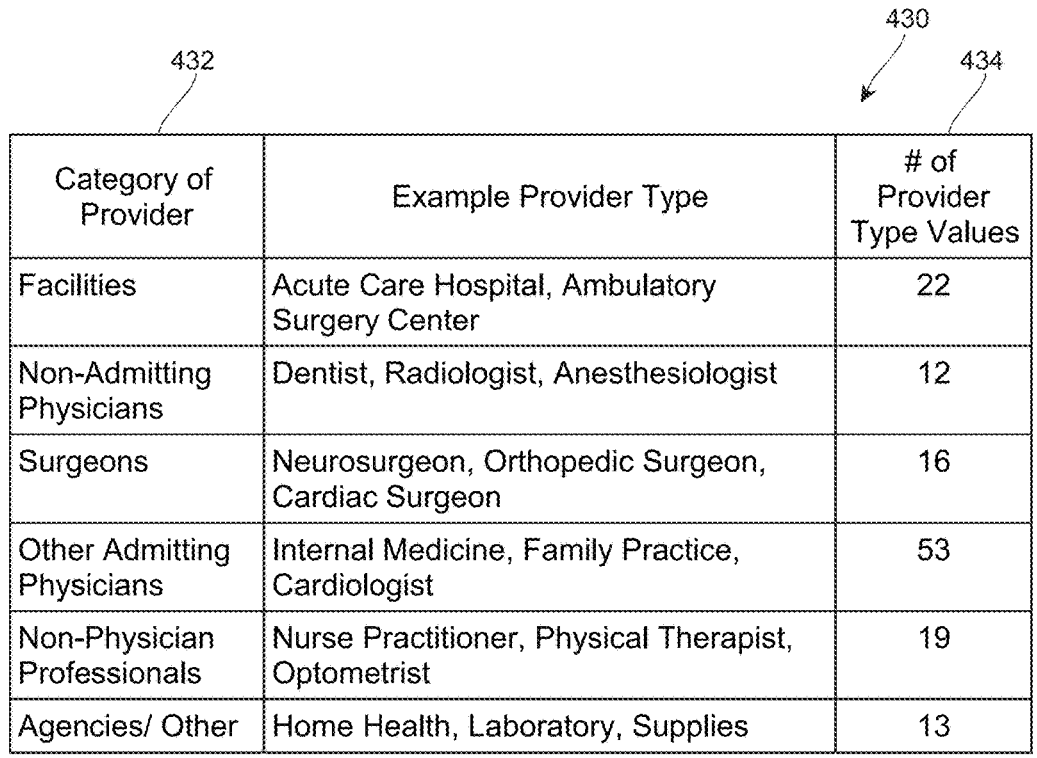

The medical claims data records may also be assigned to a provider type grouping scheme. FIG. 4D sets forth the basis of an example of a provider type categorization scheme 430 that groups all provider types into approximately 135 provider type values. The breakdown of the 135 values is shown by the "# of Provider Type Values" 434. For example, according to the example grouping scheme of FIG. 4D, 22 of the approximately 135 groupings may constitute a facility "Category of Provider" 432 provider type grouping. Referring to the example medical claims data record 300 in FIG. 3, flags related to a provider type categorization scheme may be inserted at 348. According to the example provider type categorization scheme 430, an acute care hospital would be assigned to the facilities "Category of Provider" 432 provider group. Again, as discussed in more detail below, a provider type grouping scheme may be used to map the provider type for each individual medical claims data record, which may be examined during the building of the outpatient events (step 250).

Figure 4E:
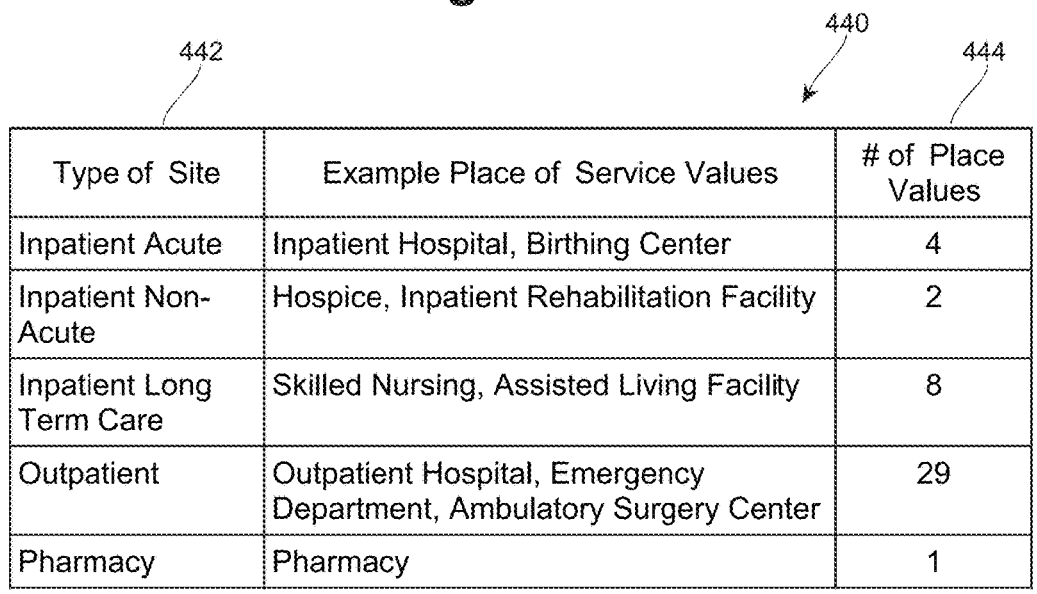

In addition, in some cases the medical claims data records may also be assigned to a place of service grouping scheme. FIG. 4E sets forth the basis of an example of a place of service categorization scheme 440 that groups standard CMS place of service codes into approximately 44 place of service value groupings. A partial breakdown of the 44 example groupings is shown by the "# of Place Values" 44 column in the chart of FIG. 4E. For example, according to the example grouping scheme shown in FIG. 4E, an inpatient acute site type represents four of the 44 values "Type of Site" 442 values. Referring to the example medical claims data record 300 in FIG. 3, flags related to a place of service categorization scheme may be inserted at 350. According to aspects of the disclosure, a place of service categorization scheme, such as place of service categorization scheme 440, may be used to map the type or place of service for each individual medical claims data record, which may be examined during the building of the outpatient events (step 250).

In some cases, each medical claims data record may be assigned a value or grouped according to all of the grouping schemes discussed above, including by the embodiments set forth above and in FIGS. 4A-4E. In other cases, however, the data may be grouped according to fewer than all of the grouping schemes set forth above or may be grouped according to other schemes as contemplated by a skilled artisan. In still other cases, however, the medical claims data records may be processed, and the outpatient events may be built, using other grouping or categorization schemes as would be contemplated by a skilled artisan.

Aggregate Claims by Date

After the medical claims data is assigned grouping or values according to one or more categorization schemes at step 220 (shown in FIG. 2), according to at least one embodiment at step 230, the medical claims data records may be grouped by date to create dateblocks. For purposes of the present disclosure, a dateblock represents a series of consecutive days, each of which includes at least one outpatient encounter, for the same patient, and may be created to account for the fact that outpatient procedures can span multiple days. While a majority of outpatient encounters occur on a single day with no related activity on the day prior or the day after, the creation and analysis of dateblocks allows for the process to include data for outpatient encounters that span across more than one day. For example, medical claims records having dates within a two-day dateblock could represent independent procedures such as two distinct office visits on two adjacent dates, or could be part of the same outpatient procedure, such as an overnight stay in observation following a surgery.

The length of each dateblock may be determined based on analysis of historical claims data identifying how long typical outpatient encounters last. In some cases for example, data may indicate that a majority of outpatient encounters span only a one-day, in which case data records would be grouped into one-day dateblocks. In other cases, it may be determined that outpatient encounters span multiple days, in which case data records would be grouped into one-day, two-day, three-day, four-day, etc., dateblocks. According to an embodiment described herein, and based on the analysis of historical claims data, dateblocks may represent one-day, two-day or three-day blocks, and dateblocks longer than three days may be treated as a series of one-day dateblocks. It should be understood, however, that in some situations, historical claims data may indicate that dateblocks be created according to different lengths, including, dateblocks for less than one day or for dateblocks of more than three days.

Figure 5:
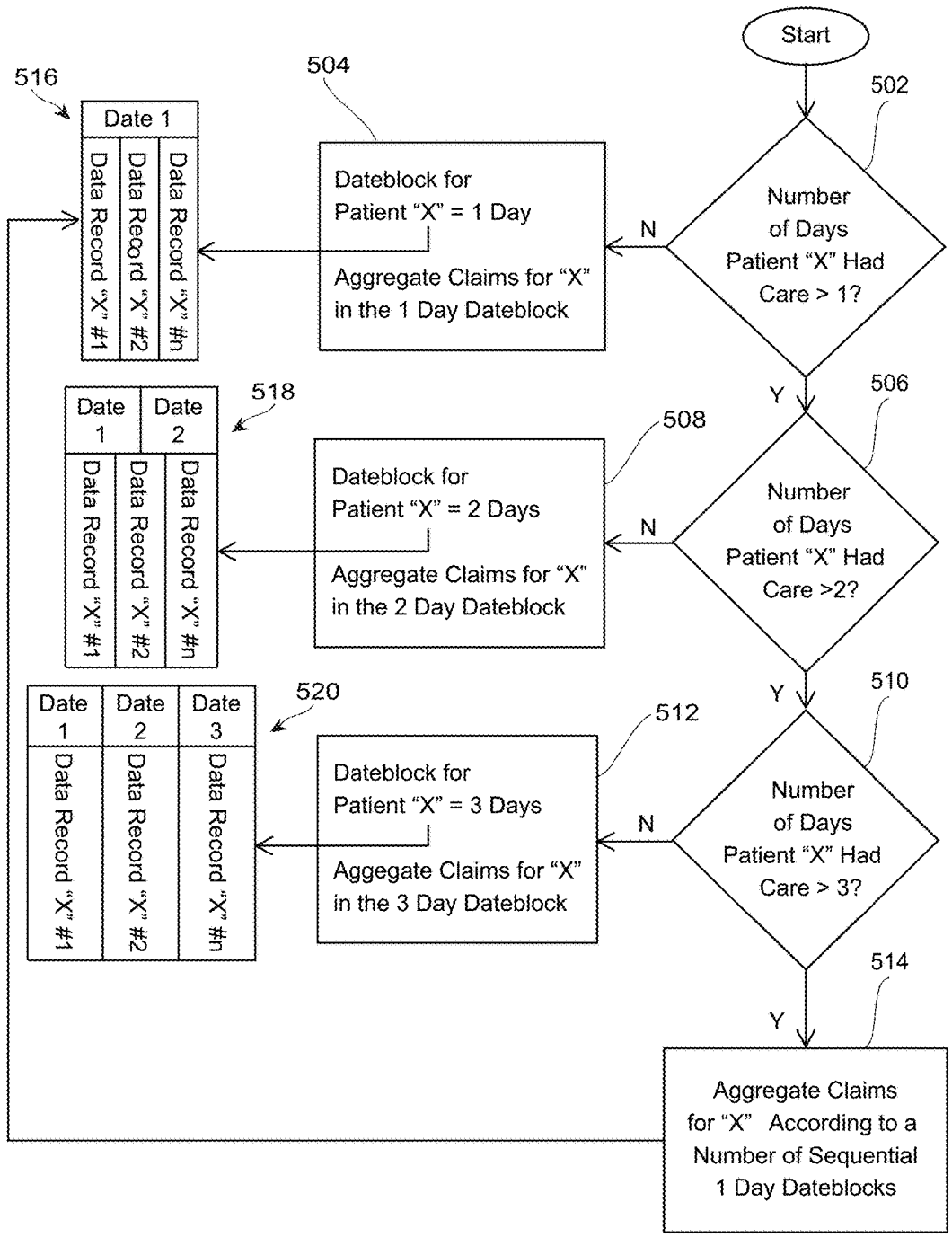
FIG. 5 depicts another flowchart of steps for grouping outpatient medical claims data, according to an embodiment of the present disclosure.

FIG. 5A depicts a flowchart of grouping medical claims data records into dateblocks according to at least one embodiment of the present disclosure. In particular, FIG. 5A depicts a flowchart of steps that may be followed in determining a dateblock for an example Patient "X." At step 502, the method examines the medical claims data records for Patient "X" to determine if the medical claims data records span more than one day. In other words, referring to the example medical claims data record 300 of FIG. 3, patient ID field 302 may be examined for Patient ID=Patient "X," along with the date of service field 308. If the medical claims data records for Patient "X" do not span more than one day, then the dateblock for Patient "X" is set to '1 Day' at step 504, and a dateblock 516 is created.

However, if the medical claims data records for Patient "X" do span more than one day, i.e., if there are more than one medical claims data records for Patient "X," and the medical claims data records for Patient "X" have more than one date of service field 308 value, the method moves to step 506. At step 506, the method examines the medical claims data records for Patient "X" to determine if the medical claims data records span more than two days. If the medical claims data records for Patient "X" do not span more than two days, then the dateblock for Patient "X" is set to '2 Days' at step 508, and a dateblock 518 is created. However, if the medical claims data records for Patient "X" do span more than two days, the method moves to step 510. At step 510, the method examines the medical claims data records for Patient "X" to determine if the medical claims data records span more than three days. If the medical claims data records for Patient "X" do not span more than three days, then the dateblock for Patient "X" is set to '3 Days' at step 512, and a dateblock 520 is created. However, if the medical claims data records for Patient "X" do span more than three days, the method moves to step 514. At step 514, for the medical claims data records of Patient "X" that span more than three days, a series of '1 Day' dateblocks are created for Patient "X," such as a series of dateblocks 516.

Prioritize Records

Once all dateblocks have been created from the historical claims data, within each dateblock, the medical claims data records may be sorted according to various parameters to determine which procedure in a dateblock should be addressed first in building the respective outpatient events. In one embodiment, the medical claims data records may be sorted by the significance of the procedures included in the claims of a dateblock. This may include identifying or determining the most significant procedure, or the procedure (identified, e.g., in procedure code field 312 of the example medical claims data record 300) having the 'highest priority,' in a dateblock. However, in other embodiments, the medical claims data records may be sorted and addressed with respect to other parameters, such as disease category or provider type.

According to step 240, in sorting the medical claims data records within each dateblock, various categorization schemes may be examined, such as the categorization schemes discussed above in relation to FIGS. 4A-4E. For example, as depicted in FIG. 4A and described above, each procedure code may be grouped into a procedure group by the type of procedure (see, e.g., type of procedure 404 of procedure categorization scheme 400). Based on the procedure group categorization according to the procedure categorization scheme 400, in at least one embodiment a priority level 402 may be assigned for the medical claims data record associated with the procedure type. Even further, according to some embodiments, the procedure groups within each priority level 402 may be sorted and assigned a priority level. In other words, within priority level '1' of FIG. 4A, the 70 procedure groups may be ordered by priority, for further sorting. For example, all major surgical procedures fall into one priority level—priority level '2' according to the embodiment of FIG. 4A, and may be ordered within that level by their estimated work effort.

In addition to the priority and sequential order, the step of identifying a sort order (step 240) within each dateblock may also take into consideration the type of record field 316, i.e., whether the data record represents a professional claim or a facility claim. This may be important because in some cases, the procedural information on professional records may be more accurate than on a facility record. Such anomalies may be accounted for by assigning a higher sort order within a particular procedure priority to a 'professional' data record.

The medical claims data records may also be sorted by the provider type (i.e. provider type field 320 of medical claims data record 300). Sorting by the provider type may ensure that within a particular procedure group, the provider most likely to accurately report the diagnosis appears first.

Figure 6A:
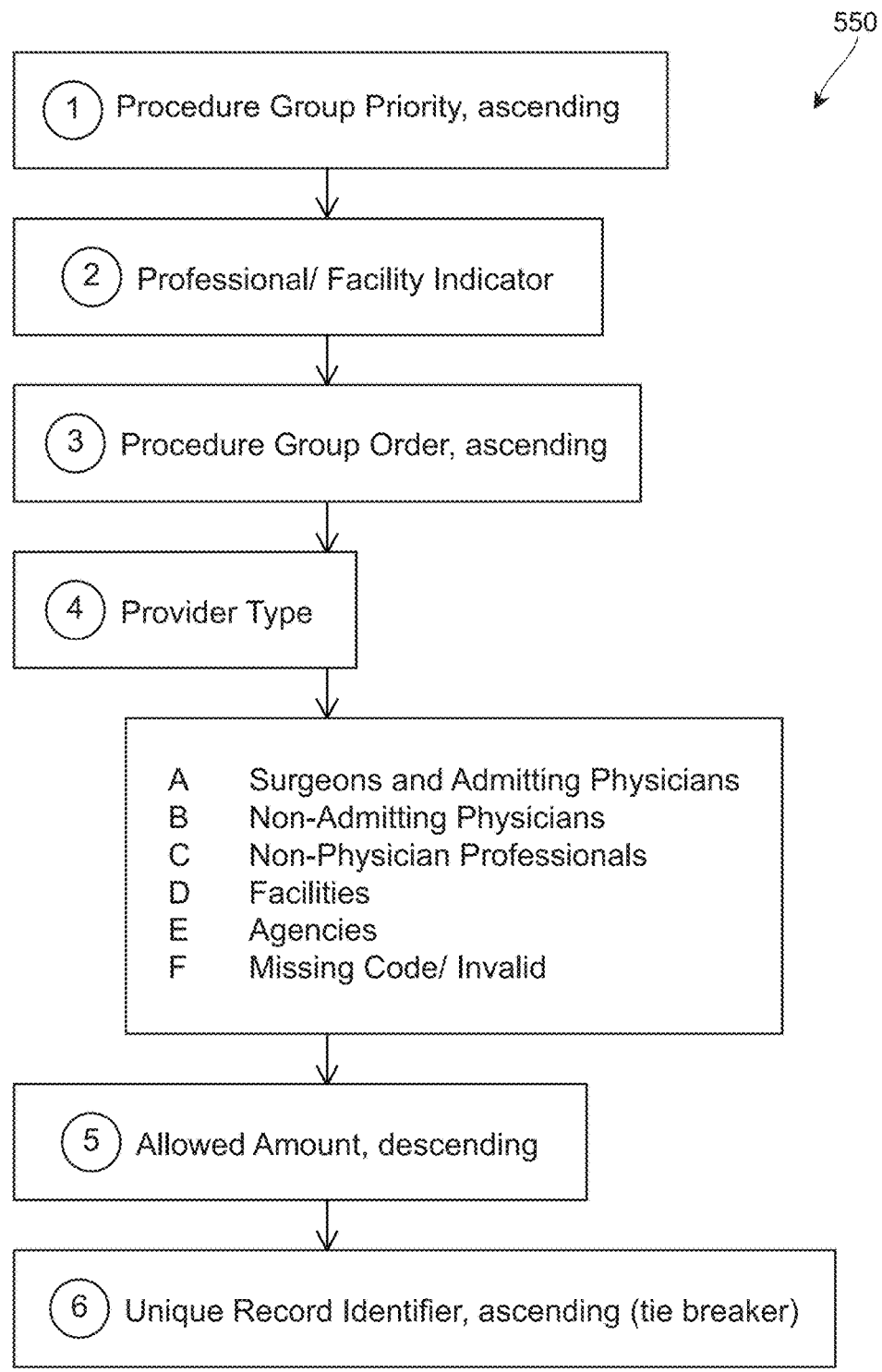
FIG. 6A depicts an example sort order for medical claims data, according to an embodiment of the present disclosure.

FIG. 6A depicts an example sort order 550, as discussed above, and according to one embodiment of the invention. In particular, during step 240, the medical claims data records within a given dateblock may be sorted in the following order to ensure the highest priority claims are addressed first: 1) by procedure group priority (ascending); 2) by the professional or facility claim type indicator; 3) by procedure group order (ascending); 4) by provider type; 5) by allowed amount (descending); and 6) by a record identifier (ascending, to serve as a tie breaker). It should be understood, however, that sort order 550 serves as one example of many possible orders, and should not be interpreted as limiting the present disclosure or other embodiments set forth herein.

Link Professional and Facility Medical Claims Data

For any given outpatient encounter, it is likely that each professional and/or facility provider involved with the outpatient occurrence may submit their own claim for payment. Accordingly, in addition to providing a sort order or priority order for the medical claims data records within each dateblock, at step 240, according to aspects of the present disclosure, the method may also create links between individual medical claims data records that represent both a professional and facility provider component of a given outpatient procedure. Linking the professional and facility components as related to a specific procedure may help to create an initial building block from which the outpatient events may be built (discussed further in relation to step 250). Furthermore, once linked as being related, the professional provider claims and the facility provider claims may remain linked during the event building step (discussed in related to step 250 of FIG. 2), and remain together in the same event, built at step 250.

A method for linking professional and facility provider claims data may use one or more baseline data sets derived from historic outpatient claims data. In at least one case, the method may analyze a baseline data set that includes a list of procedure groups which could be expected to see a corresponding separately billed professional provider claim for each facility provider claim occurrence of the procedure. Such a baseline data set may be built from historic outpatient claims data using groupings as would be known and understood in the art. In some cases, the baseline data set of procedure groups may be built from procedure groupings according to the procedure group categorization scheme 400 as described herein. However, in other cases, other procedure groupings may be used. According to at least one embodiment, the baseline data set of procedure groupings may be built by analyzing a set of historical claims data to calculate the frequency of seeing a separately billed professional provider claim when a facility provider claim is observed, and using a threshold frequency of 50% of the time for including the procedure (and procedure group) in the baseline data set of procedure groups.

In some cases, however, a medical claims data record may also lack a procedure code, and therefore a specific procedure grouping, preventing the data record from being reviewed against a baseline data set of procedure groups as described above. In such cases, the method may first analyze a baseline data set that includes a list of revenue groups which are determined to most likely be associated with one or more procedure groups in the baseline data set of procedure groups. Similar to the baseline data set of procedure groups, a baseline data set of revenue groups as described herein may be built from historic outpatient claims data using groupings as would be known and understood in the art. In some cases, the baseline data set of revenue groups may be built from both the revenue groupings according to the revenue group categorization scheme 420 and the procedure groupings according to the procedure group categorization scheme 400, as described herein. According to at least one embodiment, the baseline data set of revenue groups may be built by analyzing a set of historical claims data that includes facility medical claims having both procedure codes and revenue codes, and associating a revenue group with a procedure group if the procedure group in the set of historical claims data matches at least 95% of the time to a specific revenue group.

Figure 6B:
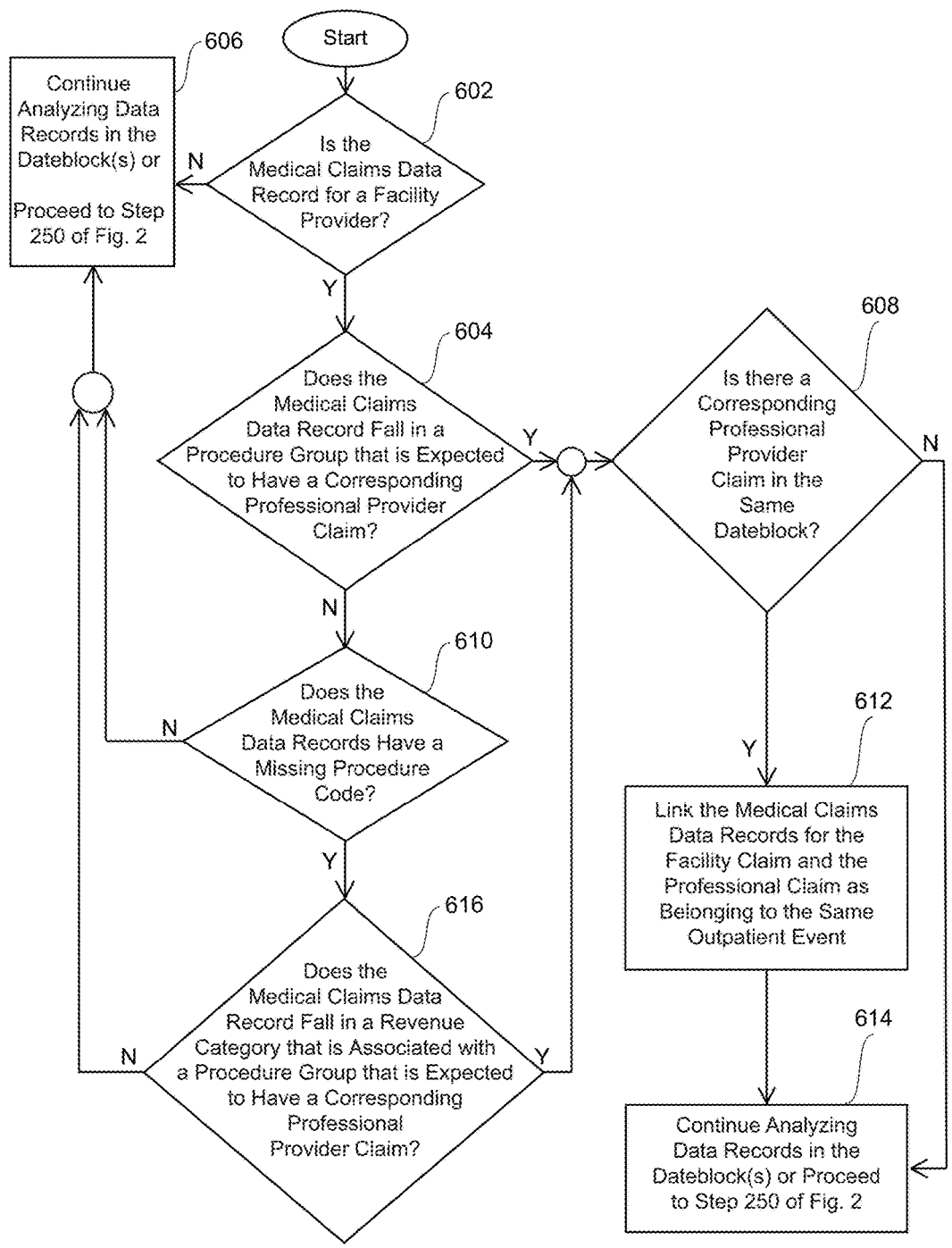
FIG. 6B depicts a flowchart of steps for linking corresponding medical claims data, according to an embodiment of the present disclosure.
Figure 6C:
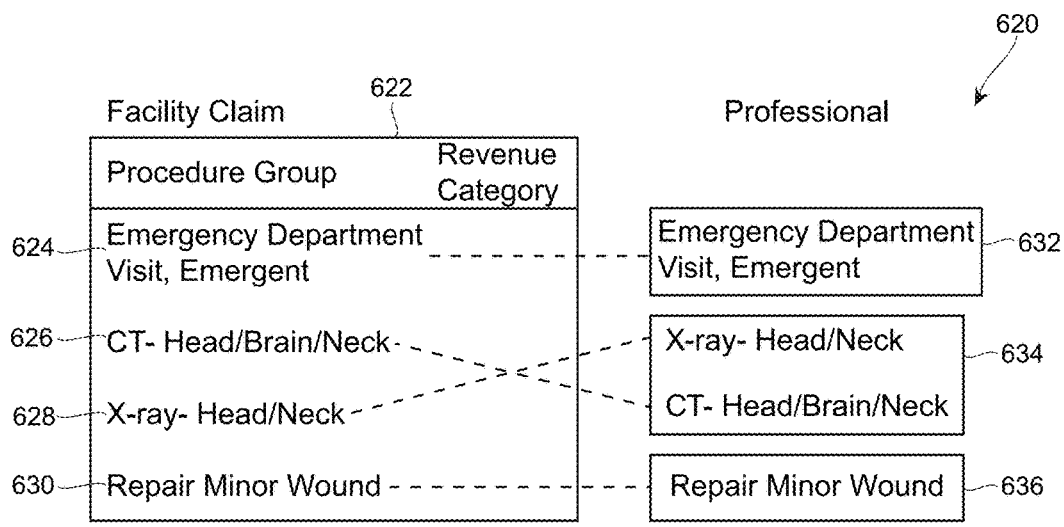
FIG. 6C-6D depict examples of methods for processing elements of medical claims data, according to an embodiment of the present disclosure.
Figure 6D:
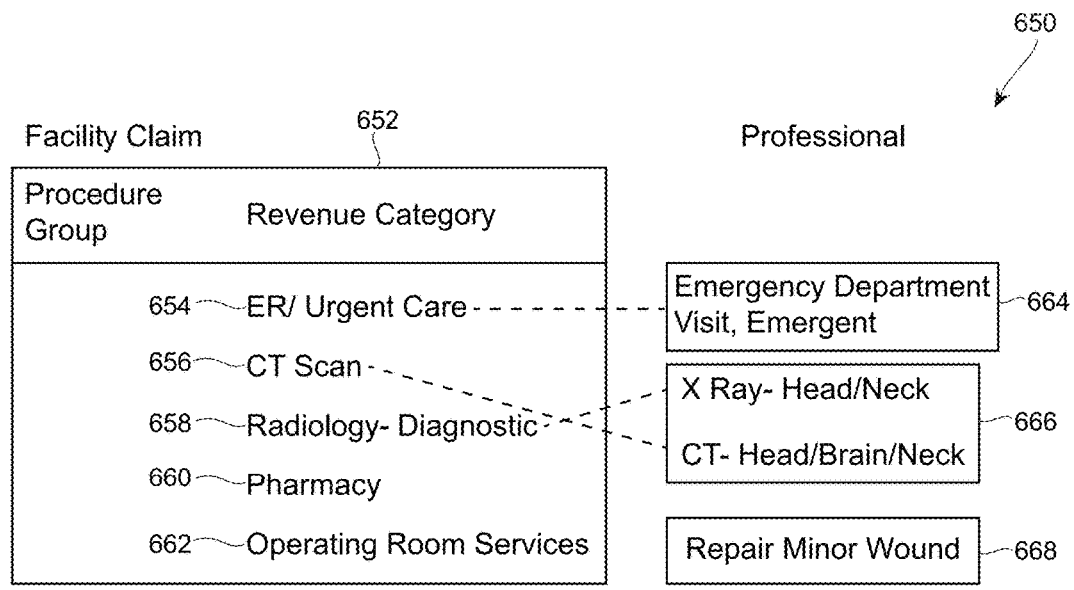
Figure 13A:
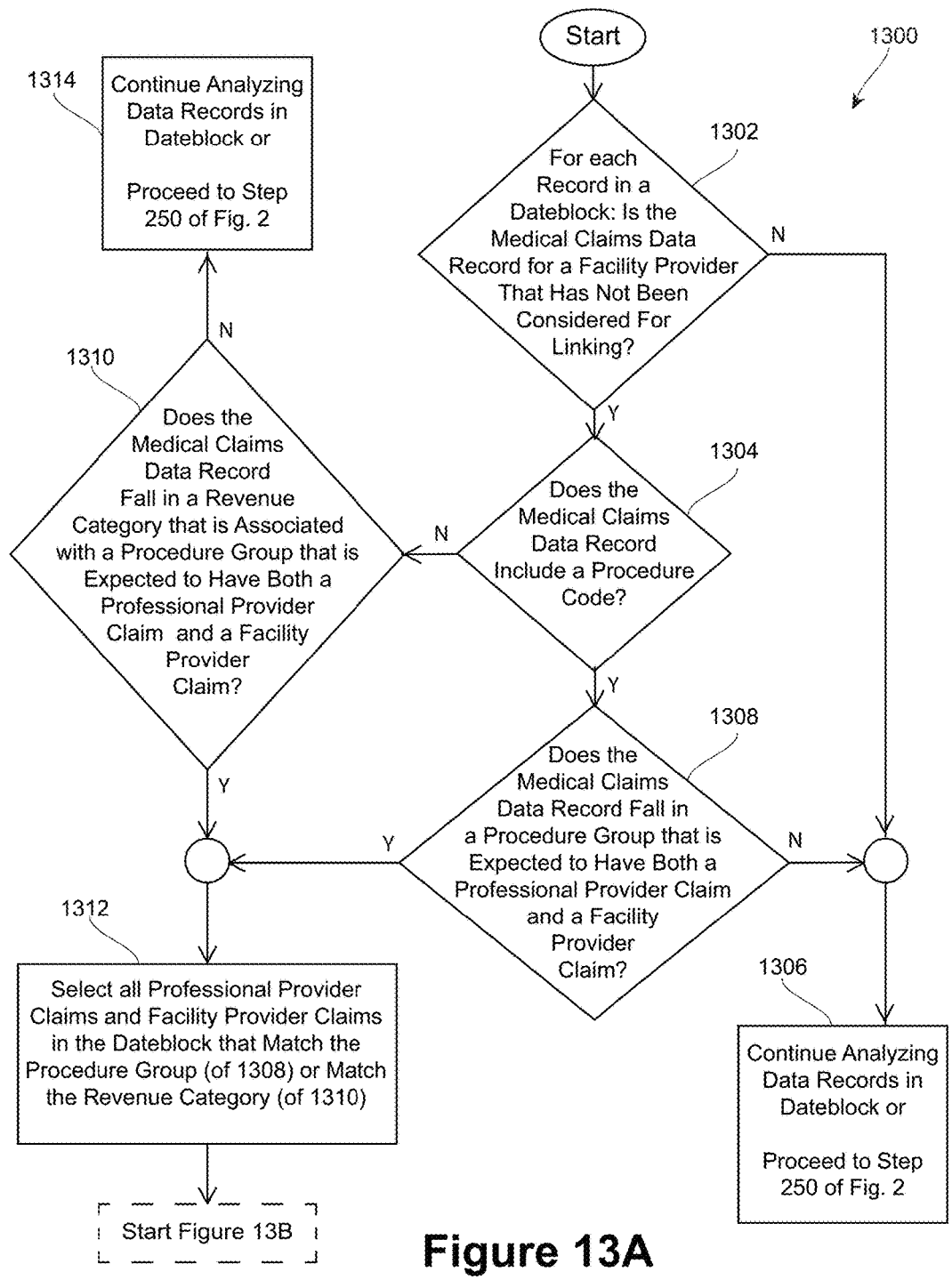
FIGS. 13A-13B depict flowcharts of steps for linking corresponding medical claims data, according to an additional embodiment of the present disclosure
Figure 13B:
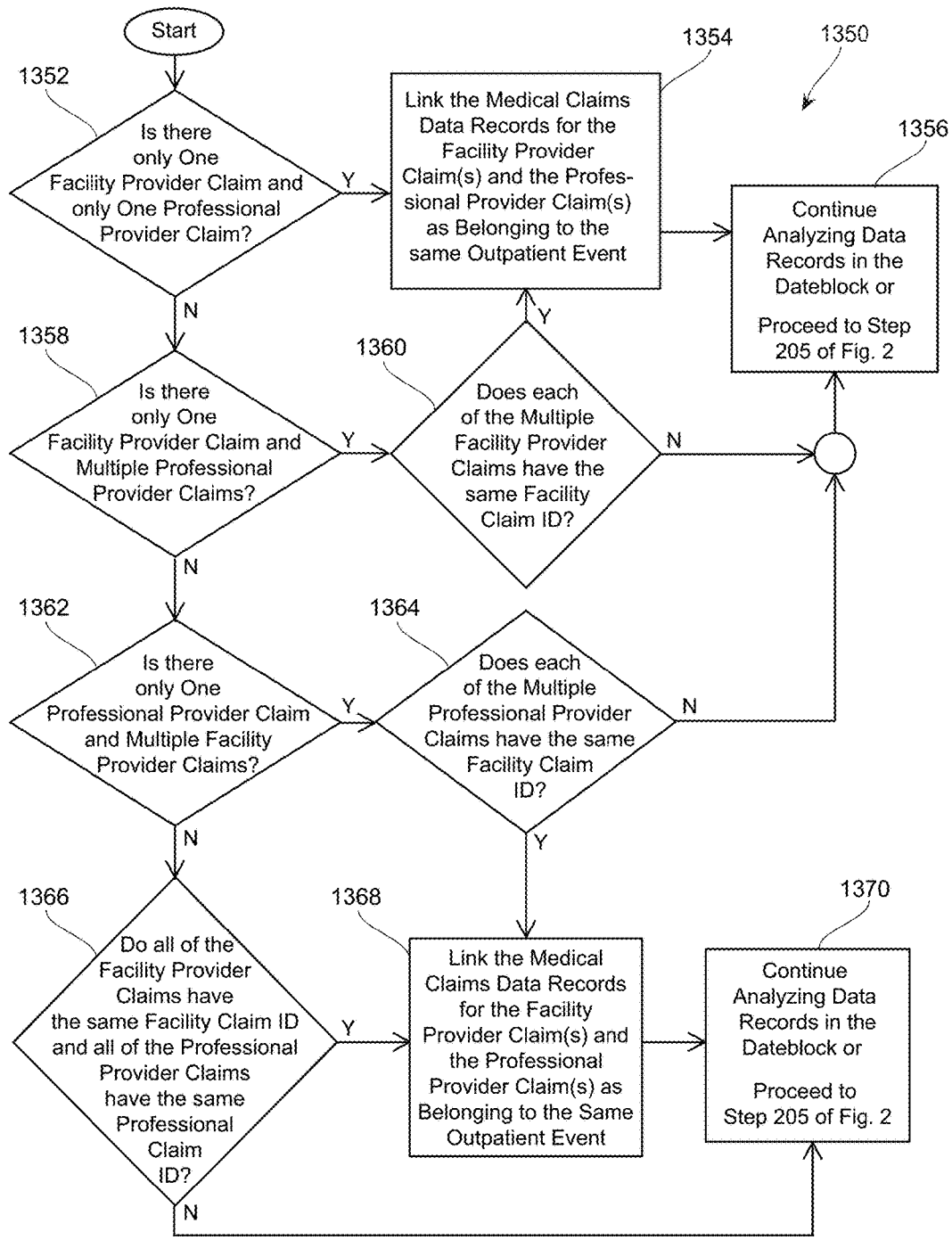

FIG. 6B depicts a flowchart of a method for linking corresponding professional and facility medical claims data records within a dateblock, according to one embodiment of the present disclosure. FIGS. 6C-6D, discussed in more detail below, depict examples of the method described herein and in in FIG. 6B. FIGS. 13A and 13B, also discussed in more detail below, depict additional flowcharts of a method for linking corresponding professional and facility medical claims data records within a dateblock, according to another embodiment. Those skilled in the art will recognize that still other methods for linking corresponding professional and facility medical claims data records are contemplated and the present disclosure is not limited to the embodiments specifically discussed herein.

Referring to FIG. 6B, the method may proceed to link corresponding facility provider medical claims data records and professional provider medical claims data records within each dateblock, until all dateblocks have been processed. At step 602, the method may review a first medical claims data record to determine if the record is for a facility record. In other words, referring to the example medical claims data record 300 of FIG. 3, claim type field 316 may be examined for claim type=facility. If the claim type is not a facility claim type, then the method proceeds to step 606, and the method either continues analyzing medical claims data records within the same dateblock, moves on to the next dateblock, or, if all dateblocks have been processed, moves to step 250 (see FIG. 2).

However, if the claim type is a facility claim type, the method moves to step 604. At step 604, the method determines if the medical claims data record falls in a procedure group that is expected to have a corresponding professional provider claim, as set forth above. If the method determines that a corresponding professional provider claim is expected at step 604, the method moves to step 608. At step 608, the method examines the dateblock to determine if the dateblock includes a corresponding professional provider claim. If a corresponding professional provider claim is not found in the same dateblock, the method proceeds to step 614, where the method either continues analyzing medical claims data records within the same dateblock, moves on to the next dateblock, or, if all dateblocks have been processed, moves to step 250 (see FIG. 2). However, if a corresponding professional provider claim is found in the same dateblock, the method continues to step 612, and flags or links the facility data record with the professional data record in the dateblock, ensuring that the claims will belong to the same outpatient event, as discussed further below.

Referring back to step 604 of FIG. 6B, If the method determines that a corresponding professional provider claim is not expected at step 604, i.e., the facility claim record does not belong to a procedure group that is expected to have a corresponding professional claim, the method moves to step 610. At step 610, the method determines if the medical claims data record in question is missing a procedure code. If the data record is not missing a procedure code, the method determines that there is not likely to be a corresponding professional claim and the process continues to step 606. However, if the data record is missing a procedure code, the method moves to step 616 where the revenue category is examined. At step 616, the method determines if the medical claims data record falls into a revenue category that is associated with a procedure group that is expected to have a corresponding professional provider claim, as set forth above. If the method determines that a corresponding professional provider claim is expected at step 616, the method moves to step 608, and continues as described above. However, if the method determines that a corresponding professional provider claim is not expected at step 616, the method moves to step 606 and continues as described above.

FIGS. 6C and 6D depict working examples of the method for linking corresponding professional and facility medical claims data records within a dateblock, according to at least one embodiment of the present disclosure, and as described above in relation to FIG. 6B. In the first example 620 depicted in FIG. 6C, a facility claim 622 for an emergency room includes procedure 624, procedure 626, procedure 628 and procedure 630. According to methods described above, it is determined that procedure 624, procedure 626, procedure 628 and procedure 630 each belong to a procedure group for which a corresponding professional bill or claim would be expected. Accordingly, facility claim 622 may be linked to professional claim 632, professional claim 634 and professional claim 636.

In the example 650 depicted in FIG. 6D, a facility claim 652 for an emergency room includes procedures that may be expected to belong to a procedure group for which a corresponding professional bill or claim would be expected, however the procedure codes are missing. Accordingly, the revenue category is used to determine a link to a professional claim. In particular, the revenue group 654 for emergency room/urgent care is linked to professional claim 664; the revenue group 656 for catscan is linked to professional claim 666; and the revenue group for radiology—diagnostic is also linked to professional claim 666. In the example 650 of FIG. 6D, however, revenue group 660 and revenue group 662 are not linked to a corresponding professional claim because the revenue categories were determined to be too broad to be linked to any of the professional claims, including the un-linked professional claim 668.

FIGS. 13A and 13B depict flowcharts of yet another embodiment for linking professional claims and facility claims within a dateblock. Similar to the embodiment of FIG. 6B, the method according to FIGS. 13A and 13B proceeds to link corresponding facility provider medical claims data records and professional provider medical claims data records within each dateblock, until all dateblocks have been processed. According to the method depicted in FIG. 13A, the medical claims data records in each dateblock may first be reviewed to determine if each claim represents a procedure that is likely to include both a professional provider claim and a facility provider claim. After the determination is made as set forth in FIG. 13A and discussed in more detail below, the method then proceeds to determine how many professional provider claims and facility provider claims exists, and whether the claims should be linked, according to the method depicted in FIG. 13B, discussed below.

Referring to FIG. 13A, at step 1302, in one embodiment, the method may first review a first medical claims data record to determine if the record is for a facility record. In other words, referring to the example medical claims data record 300 of FIG. 3, claim type field 316 may be examined for claim type=facility. If the claim type is not a facility claim type, then the method proceeds to step 1306, and the method either continues analyzing medical claims data records within the same dateblock, moves on to the next dateblock, or, if all dateblocks have been processed, moves to step 250 (see FIG. 2).

However, if the claim type is a facility claim type, the method moves to step 1304. At step 1304, the method determines if the medical claims data record includes a procedure code (see, e.g. procedure code field 312 of example medical claims data record 300 of FIG. 3). If the medical claims data record includes a procedure code, the method proceeds to step 1308. At step 1308, the method determines if the medical claims data record falls in a procedure group that is expected to have both professional provider claim and a facility provider claim. If the method determines that the relevant procedure group is not expected to have both a professional provider claim and a facility provider claim at 1308, then the method proceeds to step 1306, and the method either continues analyzing medical claims data records within the same dateblock, moves on to the next dateblock, or, if all dateblocks have been processed, moves to step 250 (see FIG. 2).

Referring back to step 1304 of FIG. 13A, if the medical claims data record does not include a procedure code, the method proceeds to step 1310. At step 1310, the method determines if the medical claims data record falls in a revenue category that is associated with a procedure group that is expected to have both professional provider claim and a facility provider claim. If the method determines that the revenue category is not associated with a relevant procedure group, and is therefore not expected to have both a professional provider claim and a facility provider claim at 1310, then the method proceeds to step 1314. At step 1314, the method either continues analyzing medical claims data records within the same dateblock, moves on to the next dateblock, or, if all dateblocks have been processed, moves to step 250 (see FIG. 2). the method determines if the medical claims data record in question is missing a procedure code.

If, at step 1308 and step 1310, it is determined that the medical claims data record falls in a procedure group that is expected to have both a professional provider claim and a facility provider claim, or falls in a revenue category that is associated with such a procedure group, respectively, then analysis proceeds at step 1312. At step 1312, all professional provider claims and all facility provider claims in the current dateblock having a matching procedure group and/or a matching revenue category (as determined at step 1308 and step 1310, respectively), are selected for further analysis according to the continuing flowchart of FIG. 13B.

After the relevant professional provider claims and the facility provider claims in the current dateblock are selected for analysis, the method proceeds to determine whether the selected claims should be linked together as being related to the same event. Referring to FIG. 13B, at step 1352, step 1358, step 1362 and step 1366, the method determines how many facility provider claims and how many professional provider claims have been selected for analysis. In particular, at step 1352, the method reviews the claims selected for further analysis and determines if there is only one facility provider claim and only one professional provider claims. If the answer at step 1352 is yes, the method proceeds to link the one professional provider claim and the one facility provider claim at step 1354, and the two claims will remain together as belonging to the same outpatient event. The method then continues to step 1356, where it continues analyzing medical claims data records within the same dateblock, moves on to the next dateblock, or, if all dateblocks have been processed, moves to step 250 (see FIG. 2).

If the answer at step 1352 is no, the method proceeds to step 1358 where it determines if there is only one facility provider claim and multiple professional provider claims. If the answer at step 1358 is yes, the method proceeds to step 1360 where it determines if each of the multiple professional provider claims has the same professional claim ID (see, e.g. claim ID field 324 of example medical claims data record 300 of FIG. 3). If the professional claim ID matches for each of the multiple professional provider claims, the method proceeds to step 1354 and step 1356 as described above. If the professional claim ID does not match for each of the professional provider claims as determined at step 1360, the method proceeds directly to step 1356.

Referring back to step 1358, if the answer is no, the analysis may move to step 1362 where it determines if there is only one professional provider claim and multiple facility provider claims. If the answer at step 1362 is yes, the method proceeds to step 1364 where it determines if each of the multiple facility provider claims has the same facility claim ID (see, e.g. claim ID field 324 of example medical claims data record 300 of FIG. 3). If the facility claim ID matches for each of the multiple facility provider claims, the method proceeds to link the multiple facility provider claims and the one professional provider claim at step 1368, and the multiple claims will remain together as belonging to the same outpatient event. The method then continues to step 1370, where it continues analyzing medical claims data records within the same dateblock, moves on to the next dateblock, or, if all dateblocks have been processed, moves to step 250 (see FIG. 2).

Referring back to step 1362, if the answer is no, the analysis may move to step 1366 where the method determines if all of the facility provider claims have the same facility claim ID and if all of the professional provider claims have the same professional claim ID. If, at step 1366, it is determined that all of the facility provider claims have the same facility claim ID and if all of the professional provider claims have the same professional claim ID, then the method links the facility provider claims and the professional provider claims as belonging to the same outpatient event at step 1368. The method then continues to step 1370, as described above. However, if the answer at step 1366 is no, the method proceeds directly to step 1370.

According to the embodiments described herein, after any professional provider claims and facility provider claims are linked together as belonging to the same outpatient event, the claims will remain together during the building of the outpatient events at step 250, described in more detail below.

Build Events

Figure 7:
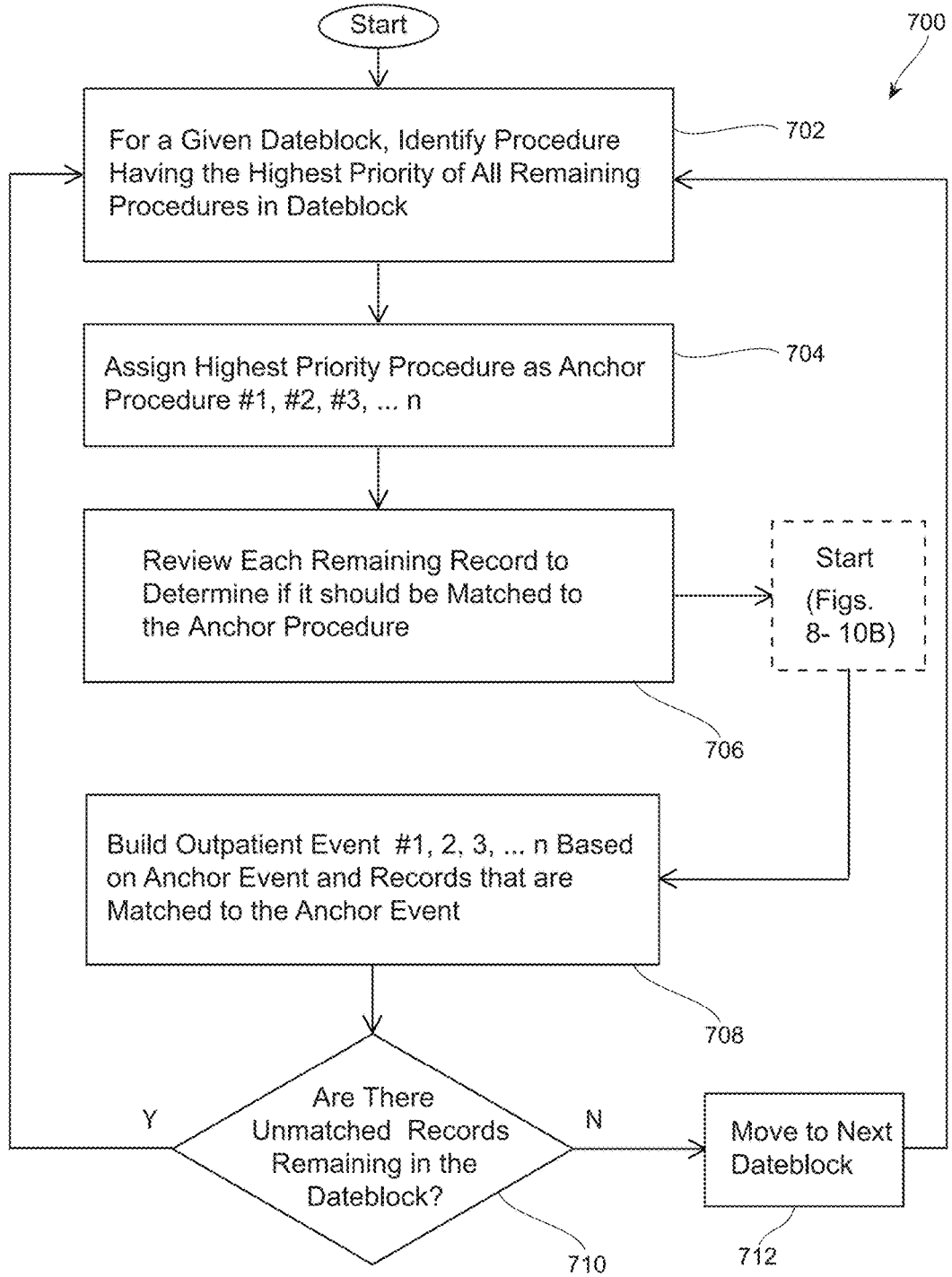
FIG. 7 depicts another flowchart of steps for grouping outpatient medical claims data, according to an embodiment of the present disclosure.
Figure 8:
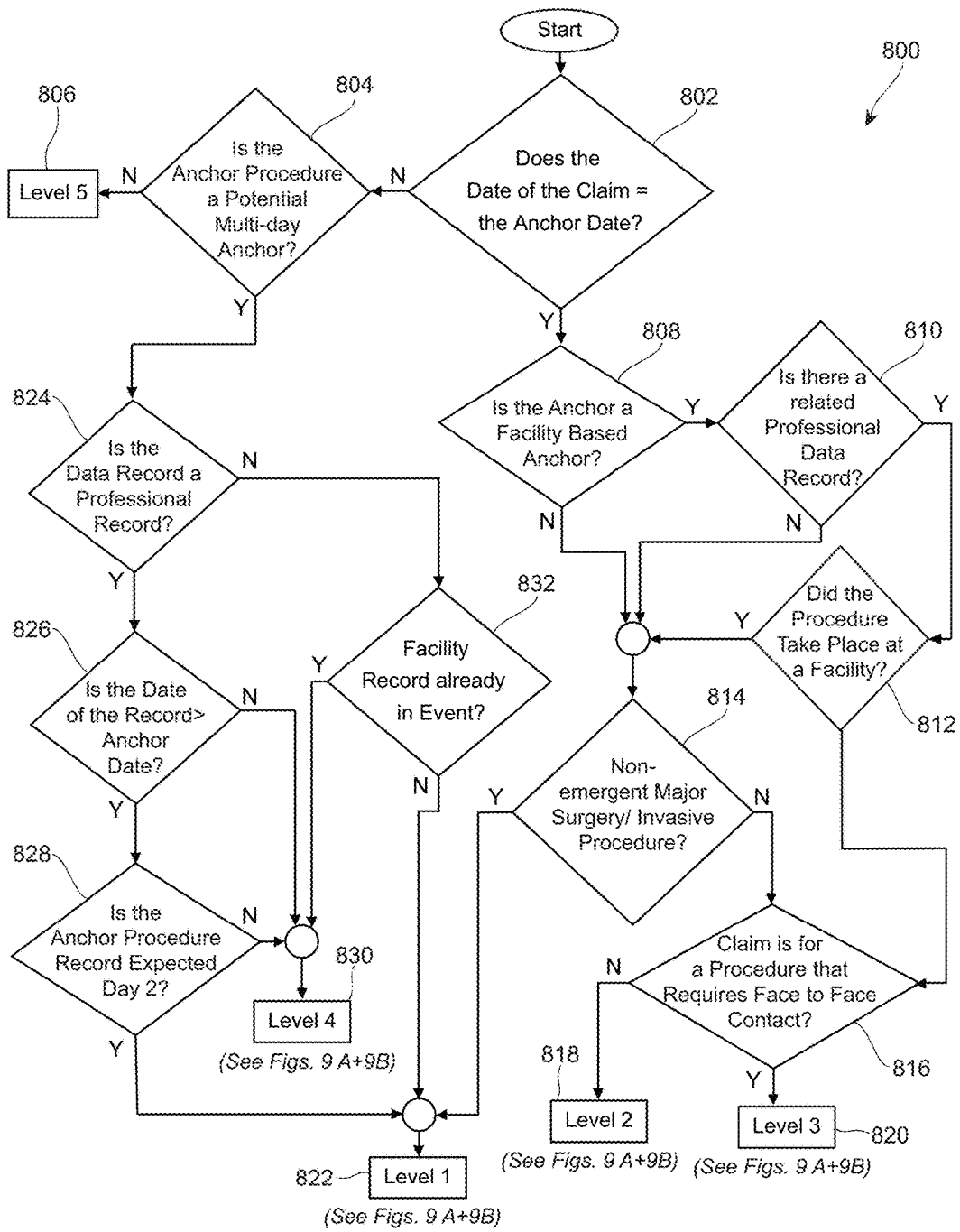
FIG. 8 depicts another flowchart of steps for grouping outpatient medical claims data, according to an embodiment of the present disclosure.

Referencing back to FIG. 2, after prioritizing and linking the medical claims data records in step 240, the method may proceed to build the outpatient events at step 250. In some cases, one or more outpatient events may be built within each dateblock. In other cases, however, a dateblock may have no outpatient events that are identified and built. As described in more detail below, and in reference to FIGS. 7-10B, methods for building outpatient events as described herein include a number of different steps and logic, each of which will be discussed in more detail below. In particular, FIG. 7 depicts a flowchart of the initial steps of identifying anchor procedures within each dateblock, wherein the anchor procedure(s) serves as the building block of each outpatient event. FIG. 8 depicts a flowchart of the steps for identifying which additional data records should be matched with the anchor procedure in building an outpatient event. FIGS. 9A-9B and 10A-10B depict additional logic that may be used in building one or more outpatient events. As set forth in more detail in relation to FIGS. 7-10B below, outpatient events may be built in an iterative fashion, assessing one dateblock at a time, and beginning with the procedure that is determined to be the most intensive, i.e. it is the procedure that is determined to have the highest priority or sort order as discussed above in relation to step 240 and using, for example, the categorization schemes set forth in FIGS. 4A-4E. As each outpatient event is built within the first dateblock, the first dateblock may be assessed to determine if any outpatient events remain to be built within the first dateblock. The process continues as further described below, moving on to the second dateblock, third dateblock, etc., until the process has assessed all of the dateblock created during step 230 of FIG. 2.

Determine Anchor Procedure(s)

According to one embodiment of the present disclosure, the process of building the outpatient events is iterative, beginning with a first dateblock and identifying an anchor procedure within the first dateblock. FIG. 7 depicts a flowchart of the steps involved in determining the anchor procedure(s) within a given dateblock, and referring to FIG. 8, matching additional medical claims data records within the dateblock to the anchor procedure, to ultimately build the outpatient event. Referring to FIG. 7, at step 702, the medical claims data records in the first dateblock may be reviewed to identify the most intensive, or 'highest priority,' procedure code. As discussed above, this may include identifying the procedure code, such as the code in procedure code field 312 of example medical claims data record 300, that is determined to have the 'highest priority' or sort order as discussed above in relation to step 240 and using, for example, the categorization schemes set forth in FIGS. 4A-4E. After identification, at step 704, the highest priority procedure code may be set as the first anchor procedure and becomes a building block for the first outpatient event in the first dateblock. Next, at step 706, the process reviews all of the remaining medical claims data records within the dateblock and evaluates each remaining record to determine if it should be included in the first outpatient event.

Whether or not each remaining medical claims data record within the dateblock is included in the first outpatient event may depend on a variety of factors, discussed in more detail below in relation to FIG. 8. However, after all of the medical claims data records in the first datablock have been reviewed to determine if they should be matched to the first anchor procedure, at step 708, the first outpatient event is built based on the first anchor procedure and all medical claims data records in the first dateblock that have been matched to the first anchor procedure. As will be discussed in more detail below in relation to FIGS. 11-12 and output record 1100 and output record 1200, relevant information such as dateblock, anchor procedure, patient, etc., may be recorded and flagged, an output record such as output record 1100 may be built, and the relevant information related to the first outpatient event may be memorialized.

Once the first outpatient event is built at step 708, the method may proceed to step 710 to determine if there are remaining medical claims data records in the first dateblock that were not matched to the first anchor procedure and thus, not included in the first outpatient event. If, at step 710, it is determined that no unmatched medical claims data records remain in the first dateblock, the process proceeds to step 712, moves to the second dateblock, and may begin the process at step 702 for the second dateblock. On the other hand, if, at step 710, it is determined that one or more unmatched medical claims data records remain in the first dateblock, the process returns to step 702 where the remaining medical claims data records in the first dateblock may be reviewed to identify the next most intensive, or highest priority, procedure code remaining in the first dateblock, and thus, the second potential anchor procedure. After identifying a second highest priority procedure code, at step 704, the next highest priority procedure code may be set as the second anchor procedure and becomes a building block for the second outpatient event in the first dateblock. The process may then continue to step 706, step 708 and step 710, as set forth above, until all of medical claims data records in the first dateblock have been included in an outpatient event built from the first dateblock. The process depicted in FIG. 7 may then be repeated in the same iterative fashion until all of the dateblocks created during step 230 (of FIG. 2) are analyzed.

Matching Logic

Whether or not a medical claims data record should be matched to the anchor procedure at step 706, and thus, included in the outpatient event being built, may be based on a number of different parameters. In some cases, whether or not a medical claims data record is matched to the anchor procedure may depend on: the date of the data record; the type of procedure identified as the anchor procedure; how the data record has been categorized according to one or more categorization schemes, such as the categorization schemes identified above and discussed in relation to FIGS. 4A-4E; statistical analysis of the strength of a relationship to the anchor procedure; whether or not certain fields in the data record match fields of other data records included in the outpatient event; and many other types of parameters that may be contemplated and implemented by a skilled artisan in the context of the present disclosure. FIGS. 8-10B depict various aspects of matching parameters and processes according to embodiments described herein. However, it should be understood that, in the context of the present disclosure, portions of the processes discussed below in relation to FIGS. 8-10B may be omitted, altered or replaced with similar techniques and still fall within the scope of the present disclosure.

The matching logic used to determine inclusion of a medical claims data record with an outpatient event may have differing levels of stringency depending on the situation. For example, if the outpatient event represents a major surgery that took place in a facility, the matching logic may be more inclusive in nature for services on the same day, based on the assumption that a patient is unlikely to have other events on the same day. In contrast, if the event is a simple MRI, the logic may be less inclusive since there is a somewhat higher probability that the patient would have other care on the same day. FIGS. 9A-9B depict various matching levels according to embodiments of the present disclosure, and specifically according to a first phase of matching logic (FIG. 9A, matching chart 900) and a second phase of matching logic (FIG. 9B, matching chart 950). In both matching chart 900 and matching chart 950, a match level 1 indicates broad matching and a match level 5 indicates stringent matching. FIG. 8 depicts a flowchart related to determining if a broad or stringent match level (e.g., levels 1-5) should be used in matching a medical claims data record to an outpatient event.

FIG. 8 depicts a flowchart that may be implemented at step 706 of FIG. 7. In particular, the process depicted in FIG. 8 may help determine whether a broad or stringent match level should be applied in matching a specific medical claims data record to an outpatient event. Continuing with the example set forth above in relation to FIG. 7, after the first anchor procedure is identified in the first dateblock, each remaining medical claims data record in the first dateblock may be reviewed based on the process of FIG. 8 to determine a matching level, and then matched or excluded from the first outpatient event based on matching chart 900 and matching chart 950 of FIGS. 9A-9B, respectively.

Referring to FIG. 8, and continuing with the example set forth above in relation to the first dateblock, the first anchor procedure, and the first outpatient event, various fields of the first medical claims data record of the first dateblock may be analyzed to determine how broadly or stringently the data record should be matched to the first outpatient event. Accordingly, at step 802, the date of the first medical claims data record (e.g., date service field 308 of exemplary record 300) may be analyzed to determine if it matches the date of the first anchor procedure. If the date does not match at step 802, the process proceeds to step 804 to determine if the first anchor procedure is potentially a multi-day procedure. If the first anchor procedure is not a potential multi-day anchor procedure, the first medical claims data record may be assigned a matching level 5 at step 806, and the process moves to a review of the matching chart 900 and matching chart 950 of FIGS. 9A-9B, discussed more fully below.

If, at step 802, the date of the first medical claims data record matches the date of the first anchor procedure, the analysis may proceed to step 808. At step 808, the first anchor procedure is reviewed to determine if it is a facility based anchor, or, in other words, if the anchor medical claims record has a facility claim type (e.g. claim type field 316 of exemplary record 300). If the answer at step 808 is yes, step 810 follows to determine if there is a related professional medical claims data record. If the answer at step 808 is no, the analysis proceeds to step 814, discussed below. Referring to step 810, it is determined if the facility claim has a corresponding professional claim. As discussed above during the process of linking the professional and facility claims, the first medical claims data record may already be linked to a corresponding professional data record, or flagged as having no corresponding professional claim. Thereafter, at step 810, if the first medical claims data record has a related professional data record, the process proceeds to step 812. At step 812, the first medical claims data record is reviewed to determine if the procedure took place at a facility, such as a hospital, or whether the procedure took place elsewhere, such as a medical office. However, if the answer at step 810 is no, the analysis proceeds to step 814, discussed below.

Referring to step 812, if the answer at step 812 is yes, i.e, the procedure took place in a facility, step 814 follows to determine if the first medical claims data record is for a non-emergent major surgery/invasive procedure. The analysis at step 814 may be based on a review of one or more of a procedure code associated with the first medical claims data record (e.g. procedure code field 312 of exemplary record 300), a procedure categorization scheme associated with the first medical claims data record, such as the example procedure group categorization scheme discussed above in relation to FIG. 4A, whether the procedure took place in an emergency department, or other factors determined to be indicative of a non-emergent major surgery/invasive procedure. If it is determined that the first medical claims data record is for a non-emergent major surgery/invasive procedure at step 814, the first medical claims data record may be assigned a matching level 1 at step 822, and the process moves to a review of the matching chart 900 and matching chart 950 of FIGS. 9A-9B, discussed below. If, on the other hand, it is it is determined that the first medical claims data record is not for a non-emergent major surgery/invasive procedure at step 814, the process proceeds to step 816.

At step 816, the first medical claims data record may be reviewed to determine if the claim is for a procedure that required face-to-face contact. This analysis may involve reviewing the provider type reported on the first medical claims data record (e.g, provider type field 348 of exemplary record 300) to determine if the provider type is one that typically reports a site of service that does not reflect a patient care location and instead reflects the provider's location. Such services often do not involve face-to-face contact, for example, laboratory services, professional radiology services, physician consultations, and medical equipment suppliers, to name a few. The answer to the analysis at step 816 then determines whether the first medical claims data record is assigned a matching level 2 at step 818 (i.e., the claim did not require face-to-face contact) or is assigned a matching level 3 at step 820 (i.e., the claim did require face-to-face contact). After step 816, process moves to a review of the matching chart 900 and matching chart 950 of FIGS. 9A-9B, discussed below.

Referring back to step 804 in the flowchart of FIG. 8, if it is determined that the anchor procedure is potentially a multi-day anchor procedure, the analysis proceeds to step 824. At step 824, the first medical claims data record is reviewed to determine if it is a professional claim type (e.g. claim type field 316 of exemplary record 300). If the answer at step 824 is yes, step 826 follows to determine if the date of the medical claims data record is later than the date of the anchor procedure record. If the date of the medical claims data record is not later than the date of the anchor procedure record, the first medical claims data record may be assigned a matching level 4 at step 830, and the process moves to a review of the matching chart 900 and matching chart 950 of FIGS. 9A-9B, discussed below. However, if the answer at step 826 is yes, the process proceeds to step 828 to determine if, based on the first anchor procedure, a claim would be expected at day 2 of the dateblock for the anchor procedure. The analysis at step 828 may include reviewing historical claims data to identify the types of services that might be expected on the day after a procedure, for example, a claim for surgical pathology, which could be expected after a surgical procedure. The answer to the analysis at step 828 then determines whether the first medical claims data record is assigned a matching level 1 at step 822 (i.e., a claim would be expected at day 2) or is assigned a matching level 4 at step 830 (i.e., a claim would not be expected at day 2).

Referring back to step 824 in the flowchart of FIG. 8, if it is determined that the data record is not a professional claim type, the analysis proceeds to step 832. At step 832, the first outpatient event is reviewed to determine if it already includes a facility claim data record. If the first outpatient event does not yet include a facility claims data record, the first medical claims data record may be assigned a matching level 1 at step 822. On the other hand, if it is determined that the first outpatient does already include a facility claim record, the first medical claims data record may be assigned a matching level 4 at step 830. Either way, the process will then proceed to a review of the matching chart 900 and matching chart 950 of FIGS. 9A-9B.

According to aspects described herein, the process depicted by the flowchart in FIG. 8 may be repeated for each medical claims data record in a dateblock to determine how strong of an association the particular medical claims data record has with the anchor procedure in the dateblock (i.e. strong, or level 1, versus not as strong, or level 2). Once the medical claims data record is assigned a level, the process of determining whether the medical claims data record should be included in an outpatient event proceeds to the matching logic and statistical analysis described further below.

FIGS. 9A and 9B depicts matching chart 900 and matching chart 950, respectively. According to at least one embodiment described herein, matching chart 900 may represent a first phase of matching logic to determine whether a medical claims data record should be matched with other data records to represent an outpatient event. If a match is not made during the first phase, the process proceeds to a second phase of matching logic, represented in matching chart 950.

As depicted in FIGS. 9A and 9B, each of the matching levels that may be assigned during the process of FIG. 8 comprise the column headings of matching chart 900 and matching chart 950. In particular, matching level 1 (step 822), matching level 2 (step 818), matching level 3 (step 820), matching level 4 (step 830) and matching level 5 (step 806) comprise the column headings of both matching chart 900 and matching chart 950. Further, the rows of matching chart 900 and matching chart 950 contain the matching logic that is applied to each medical claims data record to determine inclusion in the outpatient event, according to aspects of the disclosure. The matching logic of FIGS. 9A and 9B may be based on a variety of categorization schemes, statistical relationship tables and other methods that would be apparent to a skilled artisan in the context of the present disclosure. In some cases, the matching logic may be implemented based on statistical relationships between various categorization scheme, such as the example categorization schemes set forth above and depicted in FIGS. 4A-4E. In at least one case, the matching logic embodiments set forth in FIGS. 9A and 9B may be based on statistical relationships of medical claims data derived from historical claims data, described in more detail below, and using the categorization schemes set forth above and depicted in FIGS. 4A-4E.

According to at least one embodiment, whether a medical claims data record should be included in a particular outpatient event may be assessed according to two phases of matching logic. During a first phase, and referring to matching chart 900 of FIG. 9A, a medical claims data record, which has already been assigned a matching level during the process described above and in FIG. 8, can be assessed for inclusion based on the statistical relationship of one or more of first phase criteria 901. As depicted in FIG. 9A, first phase criteria 901 may include looking up a pre-determined statistical relationship of one or more of the following, as each relates to the medical claims data record of question and the anchor procedure/record of question: 1) the medical claims data record procedure group vs. the anchor record procedure group (902); 2) the medical claims data record principal disease category vs. the anchor record procedure group (904); 3) the medical claims data record revenue category vs. the anchor record procedure group (906); 4) the medical claims data record revenue category vs. the anchor record procedure group AND the medical claims data record disease category vs. the anchor record procedure group (908); and 5) the medical claims data record secondary disease category vs. the anchor record procedure group.

To provide an example of the matching logic of FIG. 9A, based on comparing the procedure grouping of a given medical claims data record against the procedure grouping of the anchor data record (see comparison of FIG. 9A), a statistical relationship may be determined from a statistical relationship look-up table. If the matching level for the given medical claims data record is "1" (822), the given medical claims data record may be included in the outpatient event if the statistical relationship of the procedure grouping of the given medical claims data record and the procedure grouping of the anchor data record is determined to be "related" (912). Further, if the matching level for the given medical claims data record is "2" (818), the given medical claims data record may be included in the outpatient event if the statistical relationship of the procedure grouping of the given medical claims data record and the procedure grouping of the anchor data record is determined to be "strongly related" (914). If the matching level for the given medical claims data record is "3" (820), the given medical claims data record may be included in the outpatient event if the statistical relationship of the procedure grouping of the given medical claims data record and the procedure grouping of the anchor data record is also determined to be "more strongly related" (916). Further, if the matching level for the given medical claims data record is "4" (830), the given medical claims data record may be included in the outpatient event if the statistical relationship of the procedure grouping of the given medical claims data record and the procedure grouping of the anchor data record is determined to be "very strongly related" (918). Finally, if the matching level for the given medical claims data record is "5" (806), the given medical claims data record would not be included in the outpatient event regardless of the statistical relationship of the procedure grouping of the given medical claims data record and the procedure grouping of the anchor data record (see "No" inclusion 920). Thereafter, each of comparison 904, comparison 906, comparison 908 and comparison 910 may also be made.

After all of the medical claims data records within the dateblock are evaluated for inclusion in an outpatient event as described above in relation to FIG. 9A, a second phase of matching logic may be employed. In particular, after a first statistical relationship comparison is made, secondary criteria for inclusion may be applied to the medical claims data records. The secondary criteria for inclusion may be based on a straight comparison of data fields between the given medical claims data record and other data records already included in the outpatient event. In at least one embodiment, depicted in FIG. 9B, secondary criteria 951 may include determining whether: 1) the provider ID field (e.g. provider ID field 318 in example medical claims data record 300) matches a provider ID field for any other data record already included in the event (952); and 2) the claim ID field (e.g. claim ID field 324 in example medical claims data record 300) matches a claim ID field for any other data record already included in the event (954). As depicted in FIG. 9B, comparison of one or more secondary criteria 951, may result in the inclusion of the given medical data record in the outpatient event based on the matching level that was applied to the given medical claims data record according to the process shown in FIG. 8.

Statistical Relationship Tables

The matching logic set forth herein may be based on one or more statistical relationships between various parameters, fields or categorizations of medical claims data. As would be contemplated by a skilled artisan, any number of statistical methods could be applied to historical claims data to build statistical relationship tables for application in a method such as described herein. In at least one embodiment, statistical relationships between procedures and various claim attributes may be statistically derived from MarketScan® data, for application in the methods discussed herein. Specifically, a statistical relationship table can be derived to describe the strength of observed relationships between 1) procedure groups and other procedure groups (according to a procedure group categorization scheme such as procedure group categorization scheme 400 of FIG. 4A); 2) disease categories (according to a disease category categorization scheme such as the disease category categorization scheme 410 of FIG. 4B), and 3) revenue categories (according to a revenue category categorization scheme such as the revenue category categorization scheme 420 of FIG. 4C). In particular, two categories may be considered "related", "strongly related", or "very strongly related" based on the degree of the statistical relationship seen in the analysis of the historical claims data, such as a statistical analysis of the MarketScan® data.

While a variety of known statistical analysis techniques and approaches may be used to create a statistical relationship table, in at least one embodiment, known p-value and lift ratio statistical techniques may be applied to historical claims data. In particular, when applied to historic claims data, a resulting p-value indicates whether a statistically significant relationship exists between the two procedures as observed in the data. The lower the p-value, the stronger the relationship. However, in order to account for the fact that certain procedures occur quite frequently, while others occur less frequently, a lift ratio technique may also be applied.

In order to address the potential over-inclusion that could result from using a p-value statistical technique alone, a lift ratio may be also be calculated on the pairs of procedures, as observed in historical claims data. As known in the art, the lift ratio calculation can compare an "observed" co-occurrence of procedures with an "expected" co-occurrence of procedures, where the expected value is based on the overall frequency of the procedure in the historical set of data. Higher lift ratios indicate a stronger relationship between procedures. In addition, procedures that occur very frequently will generally not have high lift values with any one particular other procedure.

To create the statistical relationships for at least one embodiment described herein, p-value and lift ratio statistics were used in combination to classify certain groupings of medical claims data records as not related, related, strongly related, or extremely strongly related. For example, in order for a disease category grouping (as understood according to one embodiment of a disease categorization scheme described herein), to be considered significantly related to a procedure category grouping (as understood according to one embodiment of a procedure categorization scheme described herein), the threshold relationship p-value was determined to be a p-value of <=0.01. To be strongly related, the threshold p-value/lift ratio was determined to be a p-value of <=0.01 and a lift ratio of >=10. To be very strongly related, the threshold relationship p-value/lift ratio was determined to be a p-value <=0.01 and lift ratio of >=30. However, it will be understood that a variety of statistical techniques may be used, and/or different threshold values may be applied, and still fall within the spirit and scope of the present disclosure.

FIGS. 10A and 10B depict examples of the p-value/lift ratio statistical analysis embodiment as applied to historical claims data of laparoscopic appendectomy procedures. In particular, FIG. 10A sets forth example statistical relationships of various procedure group relationships to laparoscopic appendectomies and FIG. 10B sets forth example statistical relationships of disease category relationships to laparoscopic appendectomies.

According to the example statistical relationship table of FIG. 10A, a column of procedure groups 1002 includes procedures groups which have been compared to the laparoscopic appendectomy procedure using a p-value statistical technique 1004 and a lift ratio statistical technique 1006. Using the example threshold values indicated above, the strongest relationships to the laparoscopic appendectomy are the procedure group itself, anesthesia and Emergency department visit groups, group 1008. In building a laparoscopic appendectomy event according to techniques described herein, group 1008 may be considered "very strongly related" and may be included in the event. Further, according to the example thresholds indicated above, lift ratios in the 10-20 range may also be considered "strongly related," and thus, in building a laparoscopic appendectomy event according to techniques described herein, group 1010 may not be included in the event based solely on the relationship of the procedure, but might require other relationship variables, such as a facility/professional link. Further down the list of FIG. 10A are items (group 1012) that are observed as co-occurring in the data, and have a significant relationship (p-value=0), but may be "less strongly related." Simply seeing items of group 1012 co-occur on the day of a laparoscopic appendectomy would not necessarily warrant their inclusion in the event, unless there was additional evidence that they were related. Finally, the bottom of the list (group 1014) includes procedure groups that, while observed with laparoscopic appendectomy in the data, have a no significant relationship to a laparoscopic appendectomy and would likely not be included in the event.

According to the example statistical relationship table of FIG. 10B, a column of disease categories 1052 includes disease categories which have been compared to the laparoscopic appendectomy procedure using a p-value statistical technique 1054 and a lift ratio statistical technique 1056. Using the example threshold values indicated above, the strongest relationships to a laparoscopic appendectomy procedure is an appendicitis 1058. However, several other gastrointestinal diagnoses, group 1060, appear frequently enough with appendectomies that they have a strong relationship to the laparoscopic appendectomy procedure. As with the procedure mapping of FIG. 10A, according to the example, lift ratios in the 10-20 range may still be "strongly related," but not as strongly as the higher lift ratios. Thus, the methods set forth herein may exercise more analytical caution when including group 1062 in the event based on the disease diagnosis alone. Group 1064, further down the list, includes diseases that are observed as co-occurring in the data, and have a significant relationship (p-value=0), but are less strongly related based on the lift ratio. Finally, disease categories toward the bottom of the list, group 1066, are those that, while observed with laparoscopic appendectomy in the data, have a non-significant statistical relationship. Accordingly, group 1066 may be considered to be extraneous items that would not be included in the event based on the disease diagnosis alone.

Create Summary Output

Referring back to FIG. 2, after the events are built for every dateblock at step 250, the method may continue to step 260 to create a summary output of the data for each outpatient event. Summary files according to the present disclosure may take a variety of forms or formats, and may include one or more data records containing aggregated information about each outpatient event created at step 250, as well as one or more cross reference files which may link individual medical claims data records to an outpatient event.

A summary output data record or file for an outpatient event may include a variety of information related to the event as well as to the number and types of medical claims data records included in the event. FIG. 11 depicts an example of a summary output data record 1100 and exemplary fields that may be included according to one embodiment. As set forth in FIG. 11, example data that may be included in an output file includes: data related to the demographic attributes of the patient 1102; data related to the general event characteristics 1104; data related to the provider(s) of the outpatient event 1106; and a variety of service type indicators 1108.

One or more cross-reference data files may also be created to link individual medical claims data records (including their record IDs) to the corresponding outpatient event. In at least one embodiment, an example of which is depicted in FIG. 12, a cross-reference file 1200 for an outpatient event may include a medical claims data record ID 1202, the procedure code 1204 and the procedure group 1206 of the medical claims data record, the sort order 1208 of the record within the event, and a reason code 1210 indicating what match logic criteria was used to include the record into the event. Such a cross-reference file may provide an easy way to view all procedures and procedure groups in a given outpatient event, or to analyze which type of matching logic is applied most frequently.

Summary output data may be used for a variety of analytical purposes, as would be understood in the art. In some cases, the output data may be incorporated into other healthcare analytic systems for broad-based analytics across multiple healthcare groups, including inpatient events and pharmaceutical events, in addition to outpatient events. In other cases, the output data may be used to analyze the outpatient data itself, including, but not limited to, the frequency of certain outpatient procedures, the efficiency of outpatient providers, payment distribution for certain procedures across providers, the frequency of co-occurring procedures, and how cost effective different providers are in providing outpatient care. Further, the summary output data may be used as input into other grouping techniques, such as medical episode grouping techniques.

In addition, while FIGS. 11 and 12 set forth examples of summary output data records that may be created for an outpatient event, it should be understood that summary output data record file 1100 and cross-reference file 1200 are only example of many types of summary files possible. In particular, other types of summary output files could contain more or fewer fields of data, or the data could be divided up into a number of different summary output files. For example, the outpatient event data could be summarized in multiple files, each file representing a category of data such as patient information, characteristics of the event, etc. In addition, summary files may be created for specific analyses, such as an analysis of diagnosis codes for an event for use in diagnostic grouping analyses. Those skilled in the art will recognize the variety of ways that summary output data may be presented about the outpatient events in the context of the present disclosure.

While various embodiments have been described, the description is intended to be exemplary, rather than limiting and it will be apparent to those of ordinary skill in the art that many more embodiments and implementations are possible that are within the scope of the embodiments. Accordingly, the embodiments are not to be restricted except in light of the attached claims and their equivalents. Also, various modifications and changes may be made within the scope of the attached claims.

What is claimed is:

1. A method for grouping medical claims data from a plurality of data sources comprising:
    receiving from the plurality of data sources, at a processor, a plurality of medical claims data records each comprising a plurality of data fields;
    sorting, at the processor, the plurality of medical claims data records by at least one grouping scheme, wherein the at least one grouping scheme examines at least one data field in each of the plurality of medical claims data records;
    building, at the processor, at least one dateblock from the plurality of medical claims data records, wherein building the at least one dateblock comprises:
        examining a patient data field and a date data field in each of the plurality of medical claims data records and grouping the medical claims data records together by a first patient and a first date; and
        sorting, by the first date, the medical claims data records grouped by the first patient into the at least one dateblock;
    prioritizing, at the processor, within the at least one dateblock, the medical claims data records according to the at least one grouping scheme to identify a first priority medical claims data record, wherein a procedure associated with the first priority medical claims data record comprises an anchor procedure for a first medical event;
    assigning, by the processor, a match level to each medical claims data record in the set of remaining medical claims data records grouped by the first patient, wherein the match level is selected from a plurality of match levels based on a plurality of matching factors;
    matching, by the processor, each medical claims data record in the set of the remaining medical claims data records to a set of the remaining medical claims data records that match the anchor procedure for the first medical event when the assigned match level is above a threshold probability level indicating that the medical claims data records are related to the anchor procedure for the medical event, wherein the probability level is derived from the strength of at least one observed relationship between medical claims data in a set of historical medical claims data;
    building, at the processor, within the at least one dateblock, the first medical event, wherein the first medical event comprises the first priority medical claims data record and the set of the remaining medical claims data records that match the anchor procedure for the first medical event; and
    applying, by the processor, the first medical event to a healthcare system analysis.

2. The method of claim 1, wherein the plurality of medical claims data records comprise outpatient medical claims data records.

3. The method of claim 1, further comprising building, by the processor, a first output data record, wherein the first output data record comprises summary information about a set of medical claims data related to the first medical event.

4. The method of claim 1, further comprising building, by the processor, a first cross-reference data record, wherein the first cross-reference data record includes a list of medical claims data records included in the first medical event.

5. The method of claim 1, wherein the at least one grouping scheme comprises grouping by procedure type.

6. The method of claim 1, wherein the at least one grouping scheme comprises grouping by a disease category.

7. The method of claim 1, wherein the at least one grouping scheme comprises grouping by a revenue category.

8. The method of claim 1, wherein the at least one grouping scheme comprises grouping by provider type.

9. The method of claim 1, wherein building dateblocks comprises:
   determining, by the processor, if the medical claims data records grouped by the first patient comprise at least one of: a one-day date; a consecutive two-day date group; or a consecutive three-day date group; and
   building, by the processor, at least one of: a one-day dateblock; a two-day dateblock; or a three-day dateblock based on the determination.

10. The method of claim 1, wherein at least one of the plurality of matching factors comprises determining if the anchor procedure is a facility-based anchor procedure.

11. A system for grouping disparate outpatient medical claims data, the system comprising:
   a database comprising outpatient medical claims data from multiple claims data sources; and
   a server coupled to the database;
   wherein, the server is further configured to:
   receive a plurality of outpatient medical claims data records from the database, each of the plurality of outpatient medical claims data records comprising a plurality of data fields;
   sort the plurality of outpatient medical claims data records by at least one grouping scheme, wherein the at least one grouping scheme examines at least one data field in each of the plurality of outpatient medical claims data records;
   build at least one dateblock from the plurality of outpatient medical claims data records, wherein building the at least one dateblock comprises:
   examining a patient data field and a date data field in each of the plurality of outpatient medical claims data records and grouping the outpatient medical claims data records together by a first patient and a first date; and
   sorting, by the first date, the outpatient medical claims data records grouped by the first patient into the at least one dateblock;
   prioritize, within the at least one dateblock, the outpatient medical claims data records according to the at least one grouping scheme to identify a first priority outpatient medical claims data record, wherein a procedure associated with the first priority outpatient medical claims data record comprises an anchor procedure for a first outpatient event;
   calculate a probability level for each of the remaining medical claims data records grouped by the first patient, wherein the probability level indicates the relation of the medical claims data records to the anchor procedure for the medical event;
   assign a match level to each of the remaining medical claims data records grouped by the first patient, wherein the match level is selected from a plurality of match levels based on a rule associated with a plurality of matching factors;
   match each medical claims data record in the set of the remaining medical claims data records to a set of the remaining medical claims data records that match the anchor procedure for the first medical event when the probability level of each assigned match is above a match threshold, wherein the match of each of the medical claims data records is limited based on an estimated accuracy of the probability level determined by comparing at least one observed relationship between medical claims data in a set of historical medical claims data;
   build, within the at least one dateblock, the first outpatient event, wherein the first outpatient event comprises the first priority outpatient medical claims data record and the set of the remaining outpatient medical claims data records that match the anchor procedure for the first outpatient event; and
   apply the first outpatient event to an outpatient system analysis.

12. The system of claim 11, wherein the server is further configured to:
   build a first output data record, wherein the first output data record comprises summary information about a set of outpatient medical claims data related to the first outpatient event;
   build a first cross-reference data record, wherein the first cross-reference data record includes a list of outpatient medical claims data records included in the first outpatient event;
   incorporate at least one of the first output data record and the first cross-reference data record into an outpatient medical claims analysis.

13. The system of claim 12, further comprising:
   an access device coupled to the server; and
   wherein the server is further configured to:
   receive, from the access device, a request for the first output data record and the first cross-reference data record;
   forward, to the access device, the first output data record and the first cross-reference data record.

14. The system of claim 11, wherein the at least one grouping scheme comprises grouping by procedure type.

15. The system of claim 11, wherein the at least one grouping scheme comprises grouping by a disease category.

16. The system of claim 11, wherein the at least one grouping scheme comprises grouping by a revenue category.

17. The system of claim 11, wherein building dateblocks further comprises:
   determining if the outpatient medical claims data records grouped by the first patient comprise at least one of: a one-day date; a consecutive two-day date group, or a consecutive three-day date group; and
   building at least one of: a one-day dateblock; a two-day dateblock; or a three-day dateblock based on the determination.

18. A non-transitory computer-readable medium comprising computer-readable instructions for performing the steps of:
   receiving from a plurality of data sources, at a processor, a plurality of outpatient medical claims data records;
   grouping, by the processor, the plurality of outpatient medical claims data records according to a procedure grouping scheme to identify a procedure type for each of the plurality of outpatient medical claims data records;
   aggregating, by the processor, the plurality of outpatient medical claims data records by date to create a plurality of dateblocks, wherein each of the plurality of dateblocks comprises a subset of the plurality of outpatient medical claims data records;
   prioritizing, by the processor, in each of the plurality of dateblocks, the respective subset of the plurality of outpatient medical claims data records;
   determining, by the processor, in each of the plurality of dateblocks, for a first outpatient medical claims data record having a facility component associated therewith, in the respective subset of the plurality of outpatient medical claims data records, whether the procedure type for the first outpatient medical claims data record falls within a set of procedure types that include both a facility component and a professional component for more than a predetermined frequency based on an analysis of historical grouped medical claims data records, wherein the predetermined frequency is based on an analysis of historical grouped medical claims data records;

linking, by the processor, in each of the plurality of dateblocks, the first outpatient medical claims data record having a facility component associated therewith to a second outpatient medical claims data record having a professional component associated therewith in the respective subset of the plurality of outpatient medical claims data records, based on the determination;

identifying, by the processor, at least one anchor procedure in each of the plurality of dateblocks, the at least one anchor procedure representing at least one of the outpatient medical claims data records in the respective subset of the plurality of outpatient medical claims data records;

applying, by the processor, matching logic to the remaining outpatient medical claims data records in the respective subset of the plurality of outpatient medical claims data records to match at least one remaining outpatient medical claims data records in the respective subset of the plurality of outpatient medical claims data records with the anchor procedure outpatient medical claims data record;

building, by the processor, at least one outpatient event comprising the anchor procedure outpatient medical claims data record and the at least one remaining outpatient medical claims data records in the respective subset of the plurality of outpatient medical claims data records; and applying, by the processor, at least one outpatient event to an outpatient system analysis.

19. The computer-readable medium of claim 18, further comprising determining, by the processor, in each of the plurality of dateblocks, for the first outpatient medical claims data record having a facility component associated therewith, in the respective subset of the plurality of outpatient medical claims data records, whether the procedure type for the first outpatient medical claims data record falls within a set of procedure types that include both a facility component and a professional component more than 50% of the time based on an analysis of historical grouped medical claims data records.

20. A method for grouping medical claims data from a plurality of data sources comprising:
receiving from the plurality of data sources, at a processor, a plurality of medical claims data records each comprising a plurality of data fields;
building, at the processor, at least one dateblock from the plurality of medical claims data records, wherein building the at least one dateblock comprises:
examining a patient data field and a date data field in each of the plurality of medical claims data records and grouping the medical claims data records together by a first patient and a first date;
sorting, by the first date, the medical claims data records grouped by the first patient into the at least one dateblock;
determining, by the processor, in the at least one dateblock, for a first outpatient medical claims data record, whether a procedure type for the first outpatient medical claims data record falls within a set of procedure types that include both a facility component and a professional component for more than a predetermined frequency based on an analysis of historical grouped medical claims data records, wherein the predetermined frequency is based on an analysis of historical grouped medical claims data records;
linking, by the processor, in the at least one dateblock, the first outpatient medical claims data record having a facility component associated therewith to a second outpatient medical claims data record having a professional component associated therewith, based on the determination;
identifying, by the processor, at least one anchor procedure in the at least one dateblock, the at least one anchor procedure representing at least one of the outpatient medical claims data records in the medical claims data records grouped by the first patient;
applying, by the processor, matching logic to the remaining outpatient medical claims data records in the medical claims data records grouped by the first patient to match at least one remaining outpatient medical claims data records in the medical claims data records grouped by the first patient with the anchor procedure outpatient medical claims data record;
building, by the processor, at least one outpatient event comprising the anchor procedure outpatient medical claims data record and the at least one remaining outpatient medical claims data records in the medical claims data records grouped by the first patient; and
applying, by the processor, the at least one outpatient event to an outpatient system analysis.

21. The method of claim 20, further comprising sorting, at the processor, the plurality of medical claims data records by at least one grouping scheme, wherein the at least one grouping scheme examines at least one data field in each of the plurality of medical claims data records.

22. The method of claim 20, further comprising determining, by the processor, in the at least one dateblock, for a first outpatient medical claims data record having a facility component associated therewith, whether the procedure type for the first outpatient medical claims data record falls within a set of procedure types that include both a facility component and a professional component more than 50% of the time based on an analysis of historical grouped medical claims data records.

23. The method of claim 20, wherein the step of determining further comprises examining, by the processor, a revenue category associated with the procedure type for the first outpatient medical claims data record.

24. The method of claim 1, wherein building the at least one dateblock further comprises:
estimating an accuracy of the probability level by comparing an observed relationship between medical claims data in a set of historical medical claims data.

25. The method of claim 24, wherein the matching of each medical claims data record in the set of the remaining medical claims data records is limited based on the estimate of the accuracy.

* * * * *